United States Patent
Glozman et al.

(10) Patent No.: US 9,402,972 B2
(45) Date of Patent: Aug. 2, 2016

(54) CATHETER ADD-ON AND METHODS OF PRODUCING AND USING SAME

(71) Applicant: Androphin Medical Ltd., Jerusalem (IL)

(72) Inventors: Yaniv Glozman, Kiryat Ata (IL); Roey Gibor, Petah Tikva (IL); Yonatan Assouline, Kfar Bilu A (IL)

(73) Assignee: ANDROPHIN MEDICAL LTD., Jerusalem (IL)

( * ) Notice: Subject to any disclaimer, the term of this patent is extended or adjusted under 35 U.S.C. 154(b) by 0 days.

(21) Appl. No.: 14/442,112

(22) PCT Filed: Oct. 30, 2014

(86) PCT No.: PCT/IB2014/065713
§ 371 (c)(1),
(2) Date: May 12, 2015

(87) PCT Pub. No.: WO2015/068085
PCT Pub. Date: May 14, 2015

(65) Prior Publication Data
US 2016/0008570 A1    Jan. 14, 2016

Related U.S. Application Data

(60) Provisional application No. 61/929,246, filed on Jan. 20, 2014, provisional application No. 61/900,047, filed on Nov. 5, 2013.

(51) Int. Cl.
*A61M 25/00* (2006.01)
*A61M 25/16* (2006.01)
(Continued)

(52) U.S. Cl.
CPC .......... *A61M 25/0017* (2013.01); *A61M 1/1008* (2014.02); *A61M 25/02* (2013.01); *A61M 25/0668* (2013.01); *A61M 5/1418* (2013.01); *A61M 25/0014* (2013.01); *A61M 2025/0098* (2013.01); *A61M 2025/0213* (2013.01); *A61M 2025/0233* (2013.01);
(Continued)

(58) Field of Classification Search
CPC ............. A61M 2025/0098; A61M 2025/0213; A61M 2025/0233; A61M 2025/0675; A61M 2207/00; A61M 25/0017; A61M 25/02; A61M 25/0668; A61M 1/1008; A61M 16/08; A61M 16/0816; A61M 16/0875; A61M 25/0014; A61M 25/0097; A61M 2209/082; A61M 2209/08; A61M 5/1418; F16L 3/22; F16L 3/13; E06B 9/326; E06B 2009/3265; Y10T 24/3982; Y10T 24/39; F16G 11/10
See application file for complete search history.

(56) References Cited

U.S. PATENT DOCUMENTS 3,621,744 A * 11/1971 Kelly ...................... B21F 11/00
                                                                        83/198
3,802,110 A *  4/1974 Guillemain ............. A01K 97/24
                                                                        43/17.2
(Continued)

FOREIGN PATENT DOCUMENTS

DK    WO 9725513 A1 *  7/1997    ............. E06B 9/326
GB       2471697 A  *  1/2011    ............. E06B 9/326

*Primary Examiner* — Adam Marcetich
(74) *Attorney, Agent, or Firm* — Skip Yarus; IPAttitude LTD.

(57) ABSTRACT

An apparatus comprising: (a) a main body adapted to engage and retain a catheter therein at a fixed point relative to the catheter length; and (b) a cutting mechanism adapted to sever said catheter in response to a pre-defined threshold force applied along the length of the catheter.

20 Claims, 18 Drawing Sheets

(51) Int. Cl.
  *A61M 1/10* (2006.01)
  *A61M 25/02* (2006.01)
  *A61M 5/14* (2006.01)
  *A61M 25/06* (2006.01)

(52) U.S. Cl.
  CPC ... *A61M 2025/0675* (2013.01); *A61M 2207/00* (2013.01); *Y10T 24/39* (2015.01); *Y10T 24/3982* (2015.01)

(56) References Cited

U.S. PATENT DOCUMENTS

| | | | | |
|---|---|---|---|---|
| 3,882,748 A * | 5/1975 | Moore | ............ | B23D 23/00 114/221 A |
| 3,962,943 A * | 6/1976 | Allen | ............ | B26D 5/38 83/360 |
| 4,813,935 A | 3/1989 | Haber et al. | | |
| 4,908,974 A * | 3/1990 | Orlick | ............ | A01K 97/24 43/17.2 |
| 5,391,148 A | 2/1995 | Bonis | | |
| 5,405,336 A | 4/1995 | Austin et al. | | |
| 5,429,620 A * | 7/1995 | Davis | ............ | A61M 3/0279 604/538 |
| 5,553,650 A * | 9/1996 | Jelic | ............ | E06B 9/326 16/442 |
| 5,577,543 A * | 11/1996 | Jelic | ............ | E06B 9/326 16/442 |
| 6,375,637 B1 | 4/2002 | Campbell et al. | | |
| 7,766,394 B2 | 8/2010 | Sage et al. | | |
| 7,766,870 B2 | 8/2010 | Dabbs | | |
| 1,007,150 A1 | 3/2011 | Gardner et al. | | |
| 8,028,466 B1 * | 10/2011 | Schrock | ............ | A01K 69/00 114/221 A |
| 2006/0161102 A1 | 7/2006 | Newcomb et al. | | |
| 2006/0167438 A1* | 7/2006 | Kalser | ............ | A61B 5/412 604/544 |
| 2007/0244468 A1 | 10/2007 | Kostandaras | | |
| 2008/0287854 A1* | 11/2008 | Sun | ............ | A61M 1/367 604/6.15 |
| 2010/0139921 A1* | 6/2010 | Birkeland | ............ | E21B 29/04 166/298 |
| 2011/0082444 A1 | 4/2011 | Mayback et al. | | |
| 2012/0302951 A1 | 11/2012 | D'Amore | | |
| 2013/0197486 A1 | 8/2013 | Aaronson et al. | | |
| 2014/0324014 A1* | 10/2014 | Lundgren | ............ | A61M 39/10 604/500 |

* cited by examiner

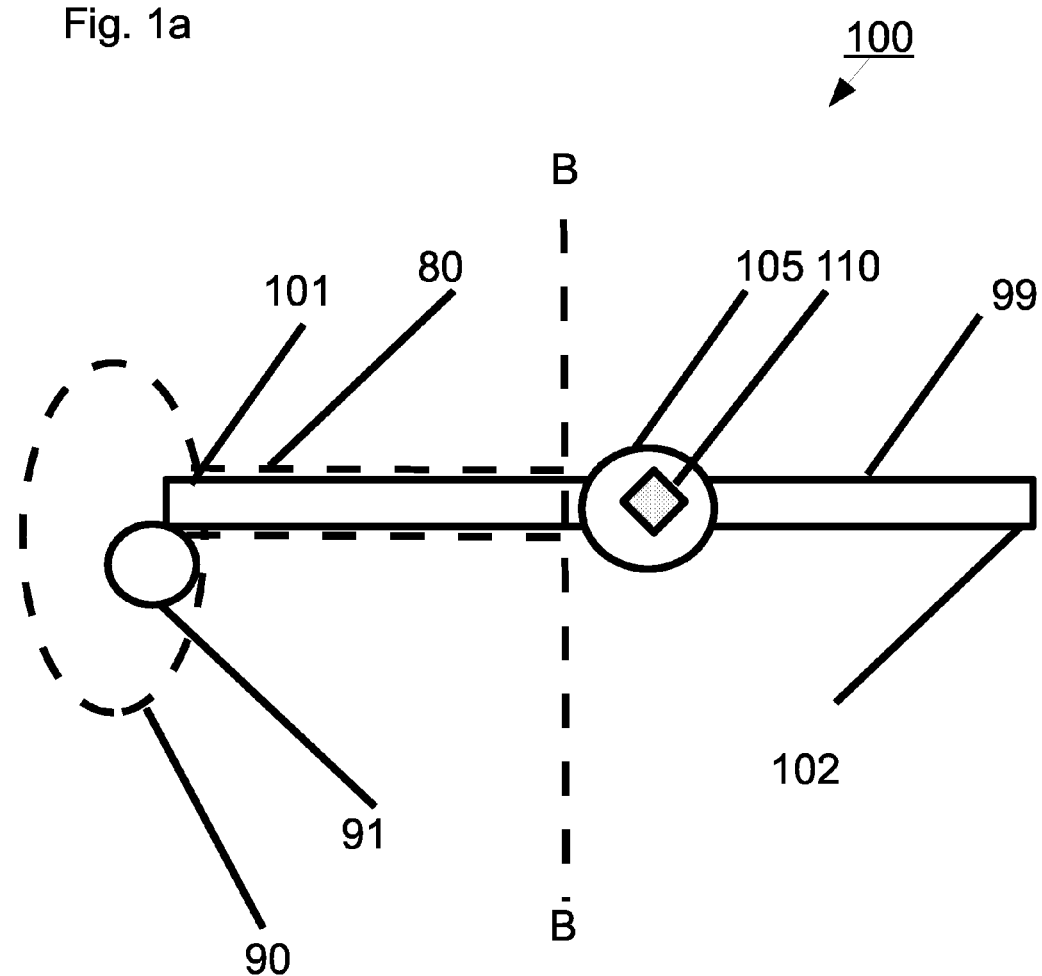

Fig. 7

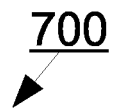

```
┌─────────────────────────────────────────┐
│ insert in-dwelling urinary catheter into │
│ bladder of patient via urethra (710)     │
└─────────────────────────────────────────┘
                    │
                    ▼
┌─────────────────────────────────────────┐
│ inflate balloon at end of catheter in    │
│ bladder (720)                            │
└─────────────────────────────────────────┘
                    │
                    ▼
┌─────────────────────────────────────────┐
│ install device comprising cutting        │
│ mechanism responsive to a pre-defined    │
│ threshold force applied along the length │
│ of the catheter at a point on the        │
│ catheter adjacent to the urethra (730)   │
└─────────────────────────────────────────┘
```

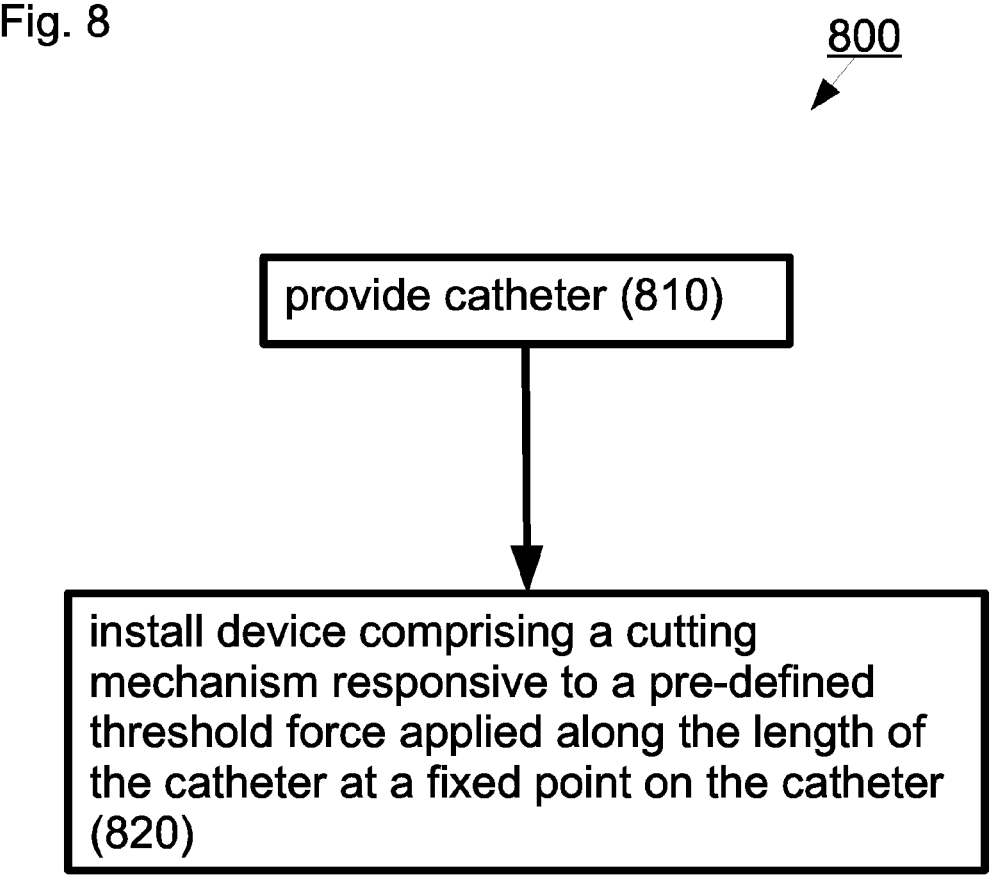

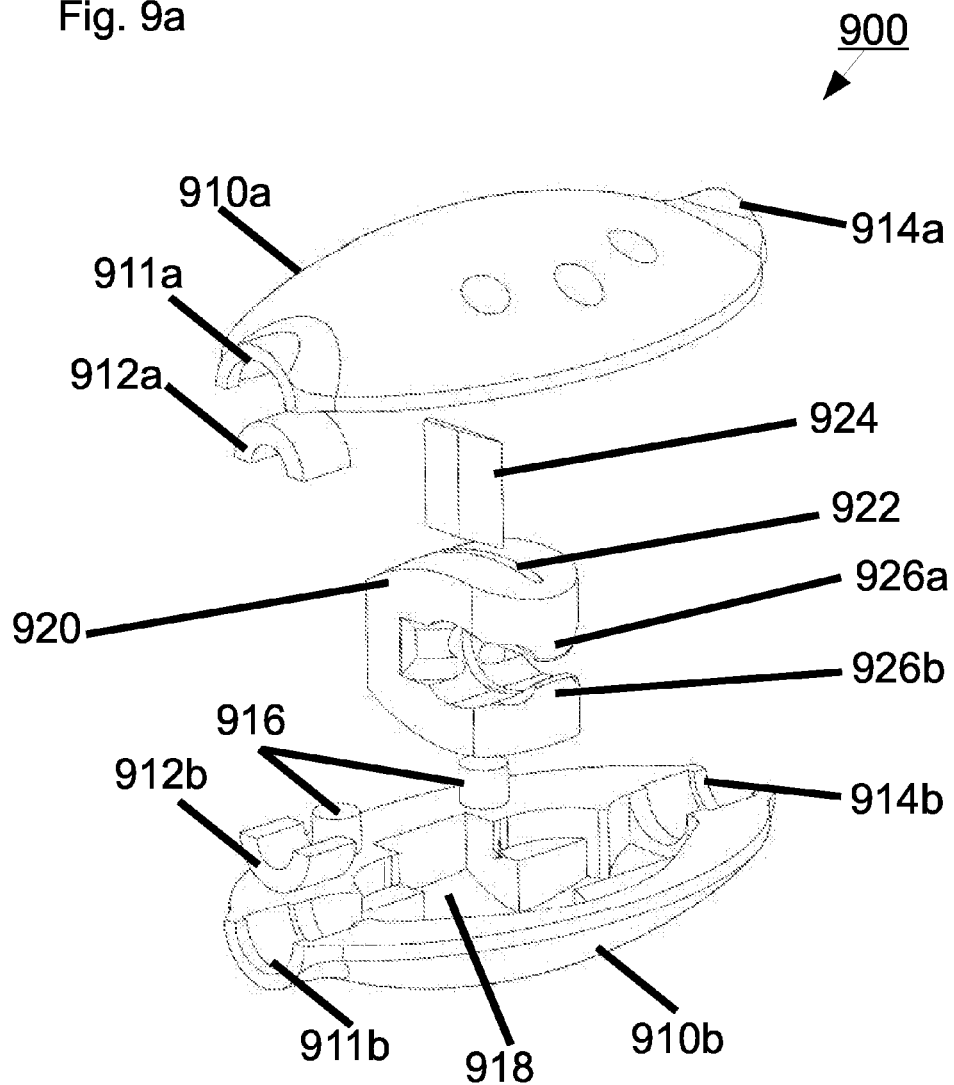

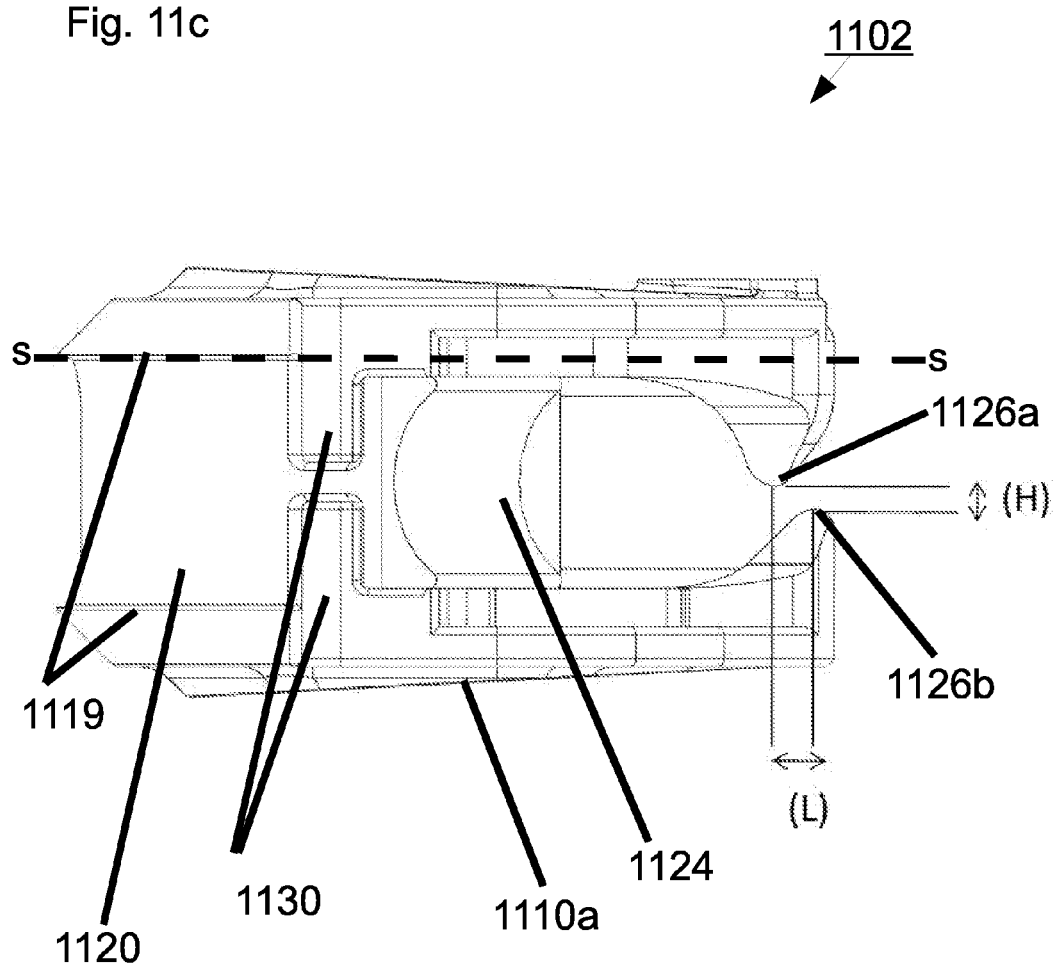

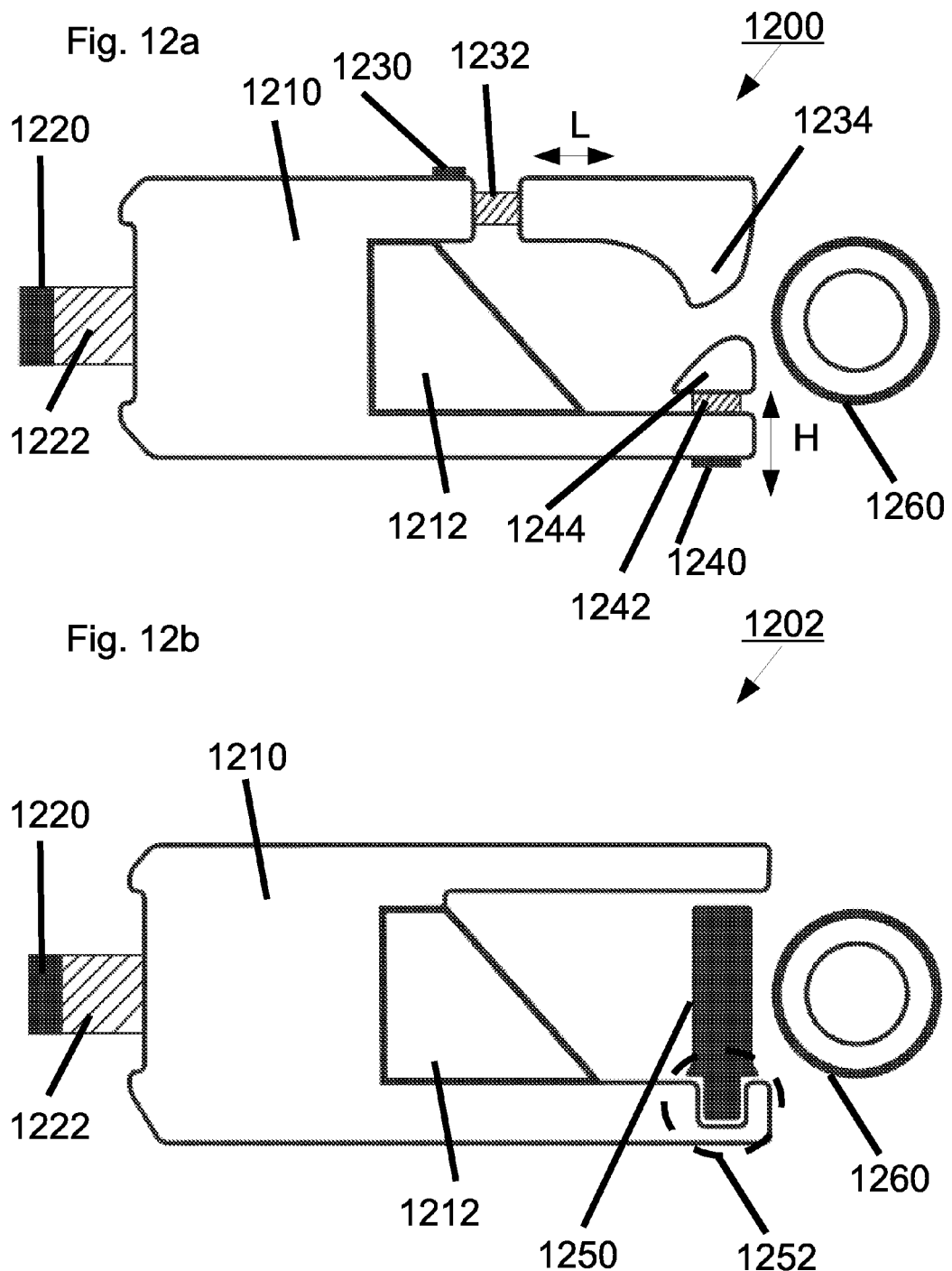

CATHETER ADD-ON AND METHODS OF PRODUCING AND USING SAME

RELATED APPLICATIONS

This application is a national stage application under 35 U.S.C. §371 of PCT/IL2008/001266 filed in 22 Sep. 2008 PCT/IB2014/065713 which claimed the benefit of 35 U.S.C. §119(e) from:

U.S. 61/900,047 filed Nov. 5, 2013 by GLOZMAN et al. and entitled "Catheter Add-On"; and U.S. 61/929,246 filed Jan. 20, 2014 by GLOZMAN et al. and entitled "Catheter Add-On and Methods of Producing and Using Same";

each of which is fully incorporated herein by reference for all that it contains.

FIELD OF THE INVENTION

Various embodiments of the invention are in the field of accessories for use with catheters.

BACKGROUND OF THE INVENTION

Urinary Catheters are used in a variety of medical contexts draining of urine from the bladder into a collection receptacle. The catheter is inserted through the urethra into the bladder. Many commonly used urinary catheters include an inflatable balloon near the end of the catheter residing inside the bladder during use. One common catheter type featuring such a balloon is the Foley catheter. Inflation of the balloon serves to anchor the catheter in place. Balloon catheters are commonly used for a variety of purposes including, but not limited to, post operative care, incontinence management and measurement of urine output.

Balloon catheters feature two inner lumens. The first wider lumen drains urine from the bladder. The second narrower lumen serves to inflate the balloon after insertion of the catheter as well as for deflation of the balloon prior to removal. Inflation is typically with sterile saline, sterile water or air.

The proximal end of the catheter (which remains outside the body) is often "Y" shaped to separate the two lumens from one another. The proximal end of the first wider lumen is often fitted with a connector for a collection vessel. The proximal end of the second narrower lumen is often fitted with an inflation valve configured to engage a syringe.

Balloon catheters are made from a variety of materials such as, for example, Teflon, Silicon, PU (polyurethane), TPU (Thermoplastic Polyurethane), PTFE (polytetrafluoroethylene), PVC (polyvinyl chloride), thermoplastic polyethylene (polyethylene TPE) or Latex and come in different sizes both by length and by diameter.

In some cases, catheters are coated with silicon, and/or hydrophilic coating and/or antimicrobial coating.

Balloon catheters are typically placed inside the urethra by medical staff (doctors and/or nurses) or para-medical care givers.

Additional catheter configurations feature three lumens.

Each year about 100 million Foley catheters are inserted in the United States and about 5 out of 100 patients attempt to remove their catheter without medical supervision (either intentionally or accidentally).

SUMMARY OF THE INVENTION

A broad aspect of the invention relates mitigating tissue damage and/or bleeding caused by removal of a catheter through the urethra while the balloon is inflated.

One aspect of some embodiments of the invention relates to placement of an "Add-On" apparatus external to the outer mall of the catheter and in close proximity to the point where the catheter enters the urethra. According to various exemplary embodiments of the invention placement occurs after the catheter is inserted, at the point of use but prior to insertion or prior to arrival at the point of use (e.g. at a manufacturing facility or in a specially designated facility within a treatment center). In some cases a catheter is inserted in one facility (e.g. a hospital) and the apparatus is installed on the catheter in a different facility (e.g. nursing home).

Another aspect of some embodiments of the invention relates to reducing a tendency towards retrograde motion of the catheter through the urethra towards the bladder. In some embodiments, the add-on apparatus, or a portion thereof) remains attached to the distal portion of the catheter (i.e. that portion inside the urethra) even if the proximal portion (i.e. outside the body) of the catheter is severed.

Yet another aspect of some embodiments of the invention relates to a cutting mechanism designed and configured to sever the proximal portion of the catheter from the distal portion in response to a pre-defined threshold force applied along the length of the catheter. According to various exemplary embodiments of the invention the pre-defined threshold force is 1.5, 2.0, 2.5, 3.0, 3.5, 4.0, 4.0, 4.5, 5.0, 5.5 or 6.0 Kgf (kilogram force) or intermediate or lesser values. One Kgf is equivalent to 9.80665 Newtons. In some exemplary embodiments of the invention, the threshold force is adjustable. In various exemplary embodiments of the invention, the threshold force is pre-set during manufacture of the add-on or determined by the user. In some exemplary embodiments of the invention, a threshold value is set according to a required end result or in accord with a catheter type. In some exemplary embodiments of the invention, the cutting mechanism employs a blade which is concealed from both the patient and the installer of the add-on on the catheter.

In some exemplary embodiments of the invention, the cutting mechanism includes a blade embedded within a resilient or spongy material. According to these embodiments, application of the threshold force causes the catheter to compress the resilient material so that the catheter wall contacts the blade and is cut by the blade. Examples of resilient material include, but are not limited to foams such as open cell foams and closed cell foams.

In some exemplary embodiments of the invention, the cutting mechanism includes a blade seated within a flexible sheath. According to these embodiments, application of the threshold force causes the catheter to flex the sheath so that the catheter wall contacts the blade and is severed or cut by the blade.

In some exemplary embodiments of the invention, the cutting mechanism includes a breakaway pin separating the catheter from the blade. According to these embodiments, application of the threshold force causes the catheter to break the pin so that the catheter wall contacts the blade and is cut by the blade. In some embodiments of this type the threshold force is isolated from the cutting force. In some embodiments of this type the cutting force is greater than the threshold force required to break the pin. In some embodiments, elasticity of the catheter contributes to this difference.

In some exemplary embodiments of the invention, the cutting mechanism includes a pair of arms with an aperture between them positioned between the blade and the catheter engaged. According to these embodiments, the aperture characteristics contribute to the threshold force level.

In some exemplary embodiments of the invention, the cutting mechanism includes a one or more blades which move in response to application of the threshold force so that the catheter wall contacts the blade(s) and is cut and/or severed by the blade. According to some exemplary embodiments of this type of cutting mechanism the blades swing away from an inner wall of a housing in which they are mounted to contact a catheter passing through the housing. In other exemplary embodiments of this type of cutting mechanism the blades are connected by a hinge and application of the threshold force causes the cutting surfaces of the blades to move towards one another through a catheter passing between them.

In all of the cutting mechanism configurations described above, application of the threshold force results in severing of the proximal portion of the catheter from the distal portion of the catheter. In some exemplary embodiments of the invention, the entire add-on remains on the end of the portion of the catheter entering the urethra. In other exemplary embodiments of the invention, a part of the add-on remains on the end of the portion of the catheter entering the urethra and another part of the add-on remains on the end of the portion of the catheter disconnected from the patient by severing.

According to various exemplary embodiments of the invention the blade(s) of the cutting mechanism is (are) integrally formed with or attached to the add-on. In some embodiments, the blade(s) are made of plastic. In other exemplary embodiments of the invention, the blades are made of metal (e.g. steel). In other exemplary embodiments of the invention, the blade(s) are made of a ceramic material. In those embodiments in which the blades are attached to the add-on, attachment can be, for example, by gluing, heat welding or use of a connector. Suitable connectors include, but are not limited to, rivets, grommets, screws, bolts and pins (e.g. cotter pin) and pegs.

In some exemplary embodiments of the invention, at least a portion of the apparatus is produced by injection molding.

In some embodiments, an add-on apparatus as described above is provided in a sterile treatment pack. In some embodiments, a catheter suitable for use with the add-on apparatus is provided as part of the same, or an accompanying, sterile treatment pack. In some exemplary embodiments of the invention, add-on apparatus and catheters are coded (e.g. color coding) to indicate which add-ons are suitable for use with which catheters. Alternatively or additionally, in some embodiments the treatment pack includes installation instructions. In some embodiments, these instructions include a series of line drawings or photographs.

Yet another aspect of some embodiments of the invention relates to methods of manufacturing add-on apparatus as described above. According to various exemplary embodiments of the invention manufacturing includes injection molding and/or thermo-forming and/or milling and/or additive manufacturing (also known as 3D printing) of at least a portion of the apparatus. Alternatively or additionally, in some embodiments manufacturing includes assembly of two or more parts. In some embodiments, the blade(s) are produced separately from other parts of the apparatus. Some exemplary embodiments of the invention, relate to molds for various portions of the apparatus.

Still another aspect of some embodiments of the invention relates to methods of use of add-on apparatus as described above.

In some exemplary embodiments of the invention, the apparatus is installed on the catheter at point of use. According to various exemplary embodiments of the invention the apparatus is installed after insertion of the catheter into the patient or just prior to insertion. In other exemplary embodiments of the invention, the apparatus is installed on the catheter at a central location within a treatment facility. In other exemplary embodiments of the invention, the apparatus is installed on the catheter at a manufacturing facility. In some embodiments, the assembled catheter/add-on is wrapped and sterilized.

Yet another aspect of some embodiments of the invention relates to methods and apparatus for testing and/or development and/or calibration of various types of apparatus designed and configured to cut a catheter in response to a force applied along the length of the catheter.

It will be appreciated that the various aspects described above relate to solution of technical problems related to undesired removal of the catheter by manual pulling of the catheter by the patients while the retention balloon is still inflated. The manual pulling may be either intentional or the result of inability to comprehend the need for the catheter (e.g. due to dementia, psychosis, retardation or youth).

Alternatively or additionally, it will be appreciated that the various aspects described above relate to solution of technical problems related to accidental removal of the catheter resulting from clinging to external objects (e.g. bed frame or IV pole) and/or accidental pulling by medical staff or caregivers (e.g. when transferring patient from a bed to a chair).

Whether removal is manual or accidental, pulling of the inflated balloon along the entire length of the urethra causes tissue damage and/or bleeding which may make it infeasible to insert a new catheter into the patient. Such tissue damage and/or bleeding is a serious clinical problem in many medical specialties including, but not limited to, pediatrics, geriatrics, psychiatric medicine and surgical recovery.

In some exemplary embodiments of the invention there is provided an apparatus including: (a) a main body adapted to engage and retain a catheter therein at a fixed point relative to the catheter length; and (b) a cutting mechanism adapted to sever the catheter in response to a pre-defined threshold force applied along the length of the catheter. In some exemplary embodiments of the invention, the pre-defined threshold force is greater than 1.5 Kgf. Alternatively or additionally, in some embodiments the pre-defined threshold force is less than 6.0 Kgf. Alternatively or additionally, in some embodiments the cutting mechanism employs a fixed blade. Alternatively or additionally, in some embodiments the fixed blade is embedded within a resilient material. Alternatively or additionally, in some embodiments the fixed blade is seated within a flexible sheath. Alternatively or additionally, in some embodiments the fixed blade is separated from the catheter by a break-away pin when the catheter is engaged and retained by the main body. Alternatively or additionally, in some embodiments the apparatus includes a pair of arms with an aperture between them positioned between the fixed blade and a catheter engaged and retained in the main body. Alternatively or additionally, in some embodiments the apparatus includes a blade holder designed and configured to hold the blade in a fixed orientation with respect to the arms and with respect to the main body. Alternatively or additionally, in some embodiments the pair of arms are integrally formed with or attached to a portion of the main body, and including a blade holder designed and configured for insertion in a corresponding socket in the main body. Alternatively or additionally, in some embodiments the cutting mechanism includes one or more blades which move in response to application of the threshold force. Alternatively or additionally, in some embodiments the one or more blades swing away from an inner wall of the main body so that a cutting surface contacts a catheter passing through the main body. Alternatively or additionally, in some embodiments the one or more blades includes two or more blades with cutting surfaces which move towards one another in response to application of the pre-defined threshold force. Alternatively or additionally, in some embodiments the apparatus includes a tensioning collar adapted to restrict axial translation of the main body with respect to a catheter retained therein.

In some exemplary embodiments of the invention there is provided a method including: (a) Fashioning a main body including engagement and retention components sized to accommodate a portion of a catheter length; and (b) Installing a cutting mechanism within the main body. In some exemplary embodiments of the invention, the method includes fashioning a socket designed and configured to engage and retain a blade holder in the main body. Alternatively or additionally, in some embodiments the method includes installing a blade in the blade holder and inserting the blade holder into the socket. Alternatively or additionally, in some embodiments the fashioning includes at least one process selected from the group consisting of injection molding, co-injection, insert injection and over molding. Alternatively or additionally, in some embodiments the fashioning includes additive manufacturing. Alternatively or additionally, in some embodiments the installing is an integral part of the fashioning. Alternatively or additionally, in some embodiments the method includes shielding at least one blade of the cutting mechanism. Alternatively or additionally, in some embodiments the shielding includes embedding within a resilient material. Alternatively or additionally, in some embodiments the shielding includes seating the at least one blade within a flexible sheath. Alternatively or additionally, in some embodiments the shielding includes installing a breakaway pin. Alternatively or additionally, in some embodiments the shielding includes positioning a pair of arms offset with respect to one another in at least two different dimensions between a blade of the cutting mechanism and the engagement and retention components. Alternatively or additionally, in some embodiments the fashioning produces two pieces configured to axially translate with respect to one another. Alternatively or additionally, in some embodiments the installing includes attachment of one or more blades. Alternatively or additionally, in some embodiments the method includes enclosing the main body with the cutting mechanism installed in sterilizable packaging material.

In some exemplary embodiments of the invention there is provided a method of treatment including: (a) inserting an in-dwelling urinary catheter into a bladder of a patient via the urethra; (b) inflating a balloon at the end of the catheter in the bladder; and (c) installing an apparatus including a cutting mechanism responsive to a pre-defined threshold force applied along the length of the catheter at a point on the catheter adjacent to the urethra. In some exemplary embodiments of the invention, the pre-defined threshold force is greater than 1.5 Kgf. Alternatively or additionally, in some embodiments the pre-defined threshold force is less than 5.0 Kgf.

In some exemplary embodiments of the invention there is provided a method of assembly including: (a) providing a catheter; and (b) installing an apparatus including a cutting mechanism at a fixed point on the catheter, the cutting mechanism responsive to a pre-defined threshold force applied along the length of the catheter. In some embodiments the pre-defined threshold force is greater than 1.5 Kgf. Alternatively or additionally, in some embodiments the pre-defined threshold force is less than 5.0 Kgf.

In some exemplary embodiments of the invention there is provided an apparatus including: (a) a main body adapted to engage and retain a catheter therein at a fixed point relative to the catheter length; and (b) a fixed blade; (c) a pair of arms positioned between the blade an inner surface of the main body; wherein a spatial relationship between the arms determines a threshold force which, when applied along the length of the catheter, causes the catheter to pass between the arms and be cut by the blade. In some exemplary embodiments of the invention, the apparatus includes a blade holder designed and configured to hold the blade in a fixed orientation with respect to the arms and with respect to the main body. Alternatively or additionally in some exemplary embodiments of the invention, the apparatus includes the pair of arms integrally formed with or attached to a portion of the main body, and a blade holder; a socket in the main body designed and configured to engage and retain the blade holder. Alternatively or additionally, in some embodiments the main body includes two halves and the arms and the blade are provided as part of a core adapted to be engaged and retained by at least one of the halves. Alternatively or additionally, in some embodiments the threshold force is greater than 1.5 Kgf. Alternatively or additionally, in some embodiments the threshold force is less than 6.0 Kgf. Alternatively or additionally, in some embodiments the apparatus includes a tensioning collar adapted to restrict axial translation of the main body with respect to a catheter retained therein.

In some exemplary embodiments of the invention there is provided an assembly including: (a) an indwelling urinary catheter; and (b) an apparatus installed on the catheter adapted to respond to a pre-determined threshold force by cutting the catheter.

Unless otherwise defined, all technical and scientific terms used herein have the same meaning as commonly understood by one of ordinary skill in the art to which this invention belongs. Although suitable methods and materials are described below, methods and materials similar or equivalent to those described herein can be used in the practice of the present invention. In case of conflict, the patent specification, including definitions, will control. All materials, methods, and examples are illustrative only and are not intended to be limiting.

As used herein, the terms "comprising" and "including" or grammatical variants thereof are to be taken as specifying inclusion of the stated features, integers, actions or components without precluding the addition of one or more additional features, integers, actions, components or groups thereof. This term is broader than, and includes the terms "consisting of" and "consisting essentially of" as defined by the Manual of Patent Examination Procedure of the United States Patent and Trademark Office. Thus, any recitation that an embodiment "includes" or "comprises" a feature is a specific statement that sub embodiments "consist essentially of" and/or "consist of" the recited feature.

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, apparatus or method.

The phrase "adapted to" as used in this specification and the accompanying claims imposes additional structural limitations on a previously recited component.

The term "method" refers to manners, means, techniques and procedures for accomplishing a given task including, but not limited to, those manners, means, techniques and procedures either known to, or readily developed from known manners, means, techniques and procedures by practitioners of architecture and/or computer science.

BRIEF DESCRIPTION OF THE DRAWINGS

In order to understand the invention and to see how it may be carried out in practice, embodiments will now be described, by way of non-limiting example only, with reference to the accompanying figures. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are:

FIG. 1a is a schematic representation of an apparatus according to various exemplary embodiments of the invention installed on a catheter deployed in a body;

FIG. 2b is a lateral cross section of an apparatus as depicted in FIG. 2a;

FIG. 7 is a simplified flow diagram of a method of treatment according to some embodiments of the invention;

FIG. 8 is a simplified flow diagram of a method of assembly according to some embodiments of the invention;

FIG. 9a is an exploded view of an apparatus according to an additional exemplary embodiment of the invention;

FIG. 11b is an exploded perspective view of the apparatus depicted in FIG. 11a;

FIG. 11c is a transverse cross section of a portion of the apparatus depicted in FIG. 11b along line S-S;

FIG. 12a is a side view of an exemplary testing apparatus; and

FIG. 12b is a side view of another exemplary testing apparatus.

DETAILED DESCRIPTION OF EMBODIMENTS

Figure 1B:
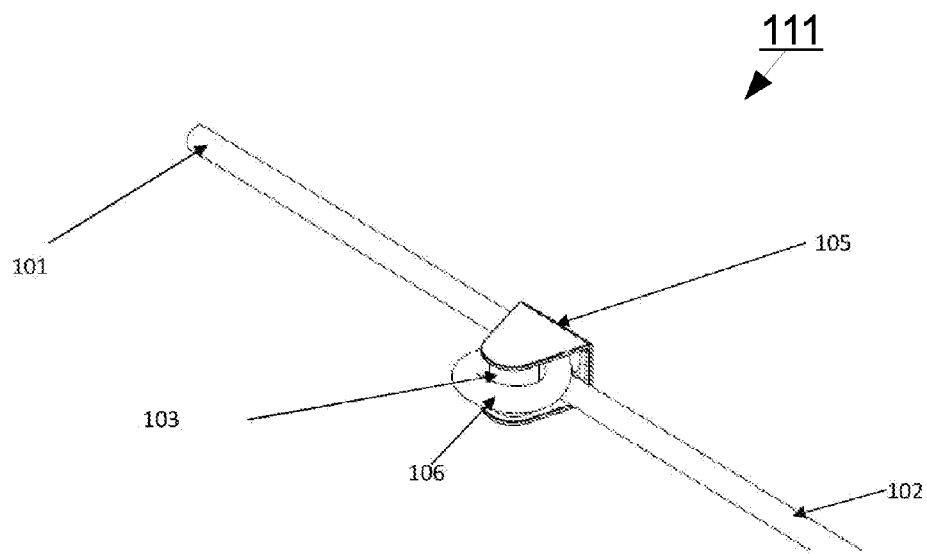
FIG. 1b is a perspective view of an apparatus according to some embodiments of the invention installed on a catheter.

Embodiments of the invention relate to apparatus for use in conjunction with a catheter and methods of producing and using such an apparatus.

Specifically, some embodiments of the invention can be used to mitigate the risk of tissue damage resulting from improper removal of a catheter. The description provided herein uses indwelling urinary catheters (e.g. Foley catheter) as an example but similar apparatus and/or methods can easily be adapted for use with other catheter types.

The principles and operation of apparatus and/or methods according to exemplary embodiments of the invention may be better understood with reference to the drawings and accompanying descriptions.

Before explaining at least one embodiment of the invention in detail, it is to be understood that the invention is not limited in its application to the details set forth in the following description or exemplified in the drawings. The invention is capable of other embodiments or of being practiced or carried out in various ways. Also, it is to be understood that the phraseology and terminology employed herein is for the purpose of description and should not be regarded as limiting.

Overview

FIG. 1a is a schematic representation of an apparatus indicated generally as 100 according to various exemplary embodiments of the invention installed on a catheter 99 deployed in a body.

In the drawing distal end 101 of catheter 99 is deployed within urinary bladder 90. A portion of catheter 99 resides within urethra 80 and a portion remains outside the body (i.e. to the right of line B-B). Proximal end 102 of catheter 99 is equipped with a fill port (not depicted) for balloon 91 and a drainage port (not depicted) for urine from bladder 90.

Depicted exemplary apparatus 100 includes a main body 105 adapted to engage and retain catheter 99 therein at a fixed point relative to the catheter length. The fixed point is select to be sufficiently close to line B-B so that any force applied along the length of catheter 99 is likely to result from engagement of main body 105 or a point on catheter 99 between main body 105 and proximal end 102 of catheter 99. According to various exemplary embodiments of the invention apparatus 100 is installed on catheter 99 so that main body 105 is less than 5, less than 4, less than 3 or less than 2 mm from line B-B. In the depicted exemplary embodiment, apparatus 100 includes a cutting mechanism 110 adapted to sever catheter 99 in response to a pre-defined threshold force applied along the length of catheter 99. This force can result, for example, from a patient grasping main body 105, or a portion of catheter 99 between 105 and 102 and pulling. Alternatively or additionally, this force can result, for example, from accidental engagement of main body 105, or a portion of catheter 99 between 105 and 102 by an inanimate object (e.g. door knob, bed rail or IV pole). In some exemplary embodiments of the invention, the pre-defined threshold force is greater than 1.5

Kgf or is greater than 2.0 Kgf. Alternatively or additionally, in some embodiments the pre-defined threshold force is less than 5.0 Kgf or less than 6.0 Kgf. In some exemplary embodiments of the invention, the predefined threshold force is about 4.6 Kgf. In some exemplary embodiments of the invention, cutting mechanism 110 employs a fixed blade. In some exemplary embodiments of the invention, cutting mechanism 110 comprises two or more blades.

First Exemplary Apparatus

Figure 1C:
FIG. 1c is a side view of the apparatus depicted in FIG. 1b.

FIG. 1b is a perspective view of an apparatus, indicated generally as 111 according to some embodiments of the invention installed on a catheter. In depicted exemplary embodiment 111 main body 105 holds the catheter in a loop 106 around a cushion of resilient material 103 (e.g. a foam). In some embodiments, loop 106 includes about 6 cm of catheter length. FIGS. 1c and 1e provide top and side views of this arrangement respectively.

Figure 1D:
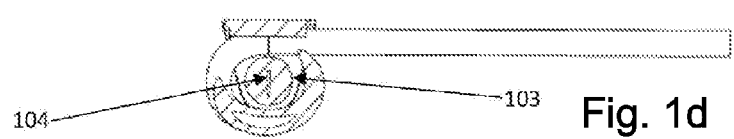
FIG. 1d is a cross section of an operative portion of the apparatus depicted in FIG. 1c through line a-a.
Figure 1E:
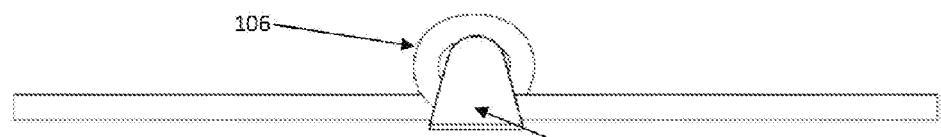
FIG. 1e is a top view of the apparatus depicted in FIG. 1b.

FIG. 1d is a cross section of an operative portion of apparatus 111 depicted in FIG. 1c through line a-a. In this cross section a fixed blade 104 is seen embedded with resilient material 103. In operation, when the predetermined threshold force is applied along the length of the catheter, loop 106 constricts and compresses resilient material 103 so that blade 104 first contacts, then severs, the catheter. Cutting of the catheter releases the force and allows resilient material 103 to expand, covering blade 104. According to embodiments of this type, blade 104 contacts only resilient material 103 (before and after application of threshold force) or the catheter (during application of threshold force). In some embodiments, main body 105 and resilient material 103 remain intact after use. Alternatively or additionally, in some embodiments, an end of the portion of the catheter extending into urethra 80 continues to be engaged by housing 105 and/or resilient material 103 after the catheter is severed.

As used in this specification and the accompanying claims the term "resilient material" includes, but is not limited to, closed cell foam or open cell foam. Some embodiments of the invention employ PU foam (polyurethane) and/or XPLE foam (cross linked polyethylene). Density of foam varies from embodiment to embodiment. In some embodiments, open cell PU foam serves as a resilient material. For example, open cell PU foam with a density of 20, 30, 40, 50, 60, 70, 80, 90, or 100 g/L or intermediate or greater values. Alternatively or additionally, in some embodiments is crosslinked PE foam (e.g. PALFOAM). For example, close cell PE foam with density of 20, 30, 40, 50, 60, 70, 80, 90, or 100 g/L or intermediate or greater values.

Second Exemplary Apparatus

Figure 2A:
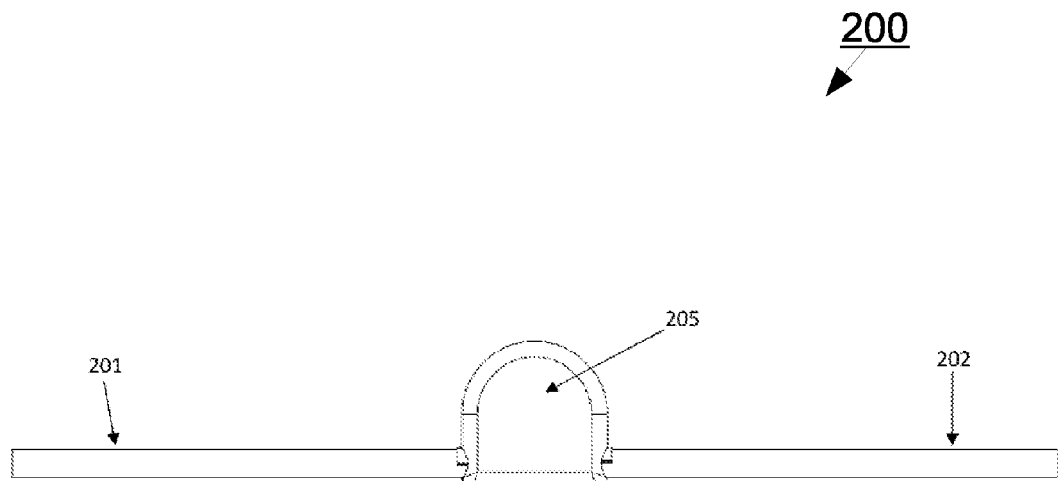
FIG. 2a is a top view of an apparatus according to additional embodiments of the invention installed on a catheter.

FIG. 2a is a side view of an apparatus, indicated generally as 200 according to additional embodiments of the invention installed on a catheter. In FIG. 2a, 201 and 202 correspond to 101 and 102 in FIG. 1a respectively.

Figure 2B:
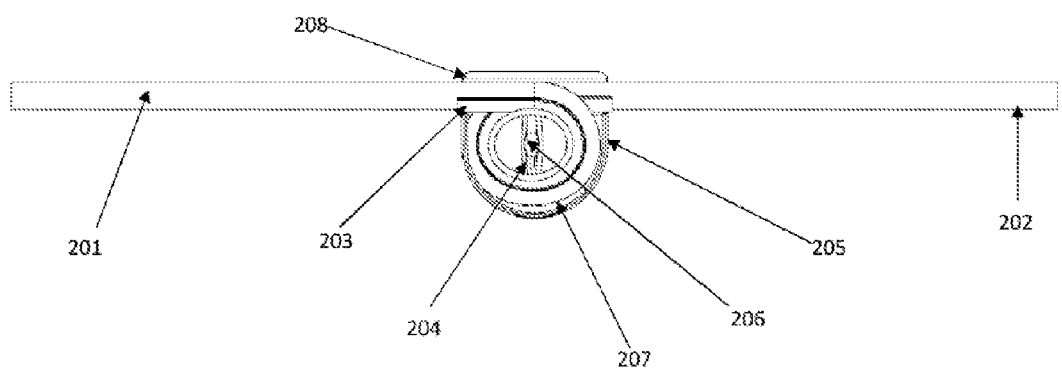

FIG. 2b is a lateral cross section of an apparatus as depicted in FIG. 2a.

Depicted exemplary apparatus 200 is similar to apparatus 101 in that it employs a cutting mechanism which relies upon one or more fixed blades. In the depicted embodiment, a single fixed blade is used. Referring now to FIG. 2b, main body 205 includes an elastic catheter channel 203 which forms a catheter loop 207 and an adhesive surface 208. According to various exemplary embodiments of the invention elastic catheter channel 203 is constructed of elastomeric polymeric material. Suitable elastomeric polymers include, but are not limited to TPU, TPE, PU, Silicon, Rubber and EPDM (Ethylene-Propylene-Diene-Monomer). The cutting mechanism of depicted apparatus 200 includes a fixed blade 204 seated within a flexible sheath 206. Function of flexible sheath 206 is similar to resilient material 103 in apparatus 101 described above. When no force is applied along the length of the catheter, sheath 206 remains extended and keeps the catheter at a distance from blade 204. Force applied along the length of the catheter causes loop 207 to contract and press on sheath 206. When the threshold pressure is reached, sheath 206 retracts by flexing. This flexing allows loop 207 to collapse onto blade 204 with sufficient force to sever the catheter. Cutting of the catheter releases the force and allows sheath 206 to expand, covering blade 204.

As used in this specification and the accompanying claims the term "flexible" indicates a value of 30A or less (ASTM D2240 type A). Suitable materials for construction of flexible sheath 206 include, but are not limited to elastic polymers such as PU and/or TPE and/or rubber and/or silicon. In some exemplary embodiments of the invention, flexible sheath 206 has a thickness of greater than 0.2, 0.4. 0.6. 0.8 or 1.0 mm or intermediate or greater thicknesses. Alternatively or additionally, in some embodiments flexible sheath 206 has a thickness of less than 2.0, 1.8, 1.6, 1.4, 1.2 or 1.0 mm or intermediate or lesser thicknesses.

Third Exemplary Apparatus

Figure 3A:
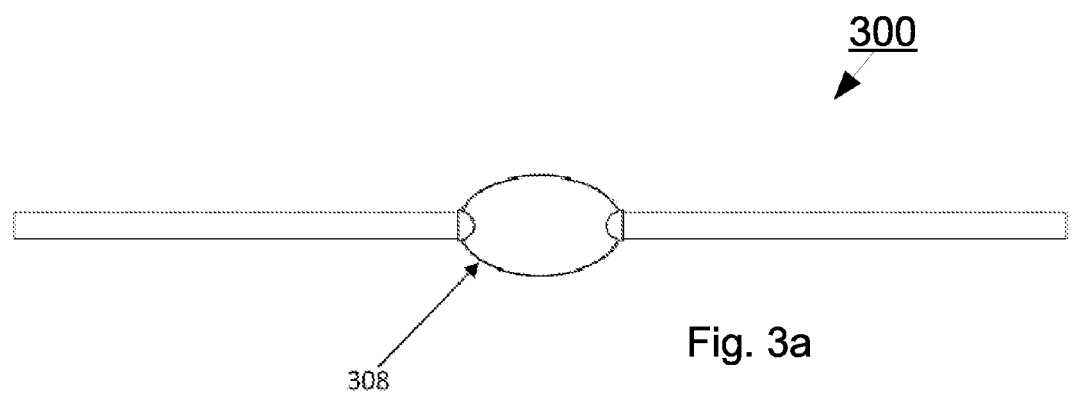
FIG. 3a is a top view of an apparatus according to further additional embodiments of the invention installed on a catheter.

FIG. 3a is a top view of an apparatus, indicated generally as 300, according to further additional embodiments of the invention installed on a catheter.

Figure 3B:
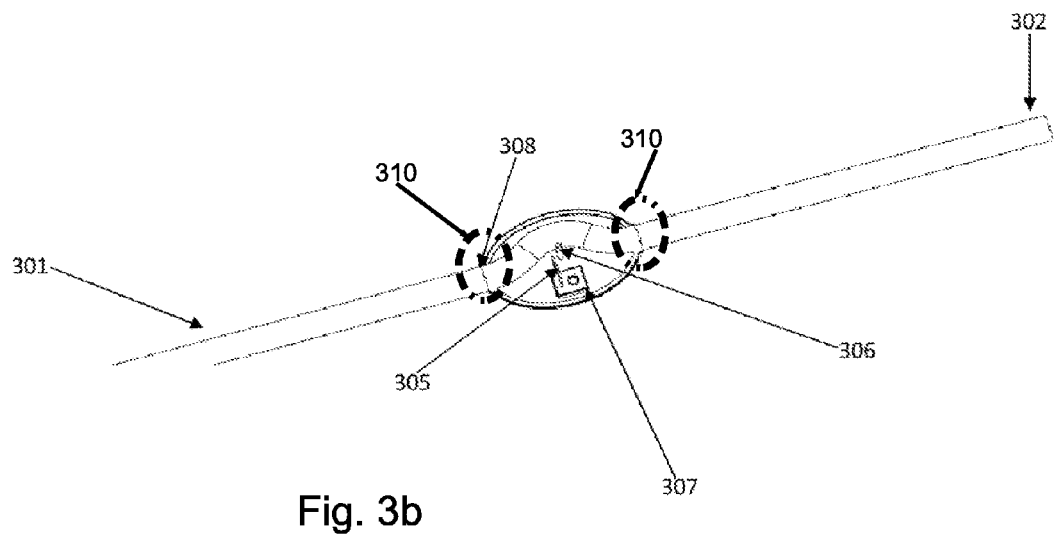
FIG. 3b is an elevated view of the apparatus as depicted in FIG. 2a with functional components exposed.

FIG. 3b is an elevated view of apparatus 300 with functional components exposed. In the drawing, 301 and 302 correspond to 101 and 102 in FIG. 1a respectively.

Depicted exemplary apparatus 300 is similar to apparatus 101 in that it employs a cutting mechanism which relies upon a fixed blade. Referring now to FIG. 3b, main body 308 contains a fixed blade 305. In the depicted exemplary embodiment, blade 305 is mounted on a blade support 307. In other exemplary embodiments of the invention, blade 305 is integrally formed as part of main body 308. The catheter passes through main body 308 via two catheter ports 310. During installation, the catheter is bent slightly so that break-away pin 306 prevents contact between the catheter and blade 305. In some embodiments, an adhesive applied to the apparatus and/or the catheter keeps the apparatus attached to the distal portion of the catheter (in the body) after the catheter is severed. This attachment by adhesive contributes a reduction in the likelihood that the distal portion of the catheter will be drawn into the body.

As long as no force is applied along the length of the catheter, blade 305 is separated from the catheter by break-away pin 306 while the catheter is engaged and retained by main body 308. A threshold force applied along the length of the catheter pin 306 to break. When pin 306 breaks, the catheter straightens, contacts blade 305 and is severed. Cutting of the catheter releases the force. In embodiments of this type, the blade is shielded only by main body 308. Alternatively or additionally, in embodiments of this type pin 306 sets the threshold force. For example, increasing the diameter of pin 306 increases the required threshold force. As a detailed example, for a catheter 16 French latex catheter, to achieve a threshold force of 2 Kgf a pin 306 made of PC (Polycarbonate) will have a thickness of 1.2 mm. In some embodiments, in order to adapt device 300 for a catheter with a wider diameter, thickness of pin 306 also increases. Alternatively or additionally, in some embodiments an increase in a diameter of pin 306 serves to increase the threshold force a catheter of a given diameter. Alternatively or additionally, according to various exemplary embodiments of the invention the material used to fashion pin 306 contributes to the threshold force.

All of the apparatus described hereinabove employ a fixed blade and rely upon motion of the catheter relative to the blade to sever the catheter.

Additional embodiments of the invention relate to apparatus which contain a cutting mechanism including one or more blades which move in response to application of the threshold force to the catheter.

Additional Exemplary Apparatus

Figure 9B:
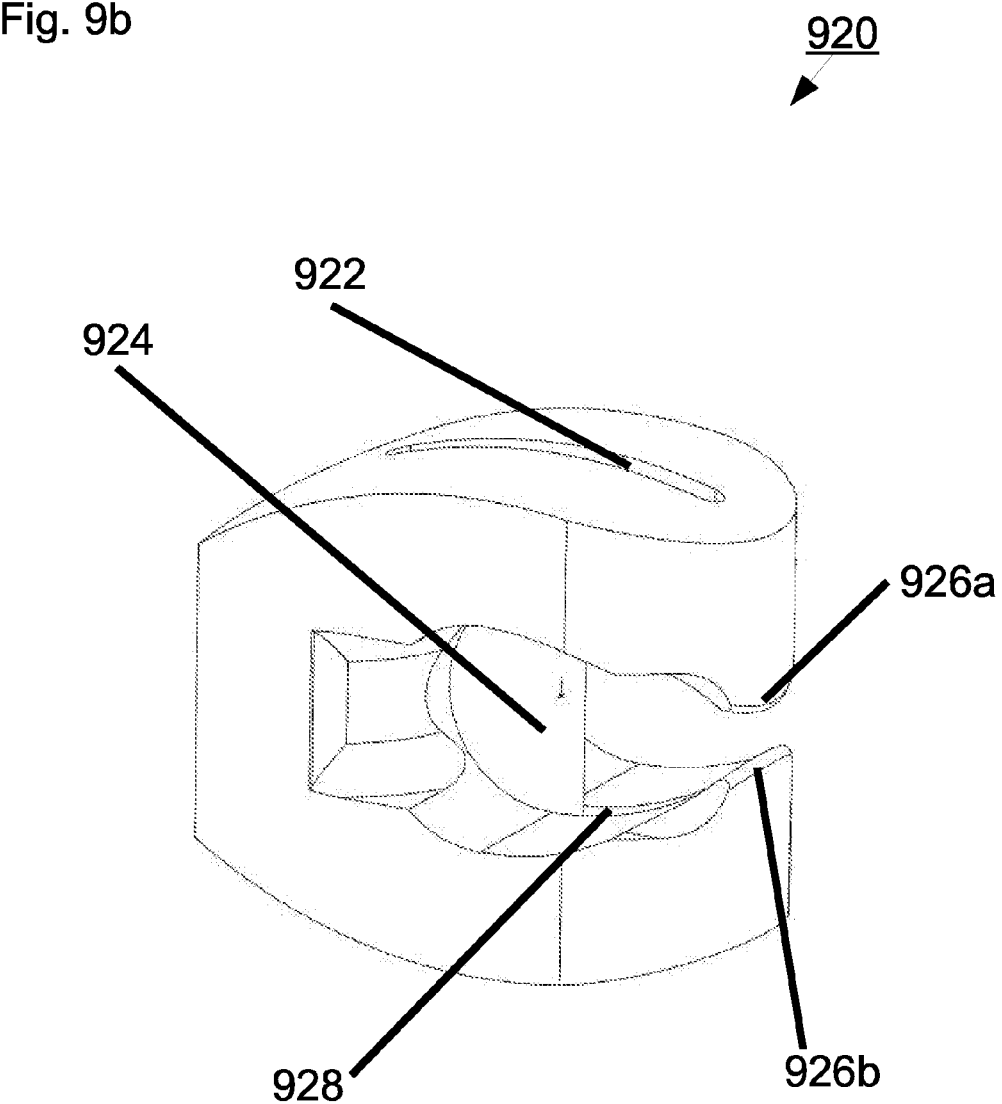
FIG. 9b is a perspective view of the cutting mechanism of the apparatus depicted in FIG. 9a with a blade inserted.

Three additional exemplary apparatus are depicted in FIGS. 9a and 9b; FIG. 10 and FIGS. 11a, 11b and 11c.

FIG. 9a is an exploded view of an apparatus according to an additional exemplary embodiment of the invention indicated generally as 900.

FIG. 9b is a perspective view of the cutting mechanism 920 of apparatus 900 with a blade 924 inserted.

Figure 10:
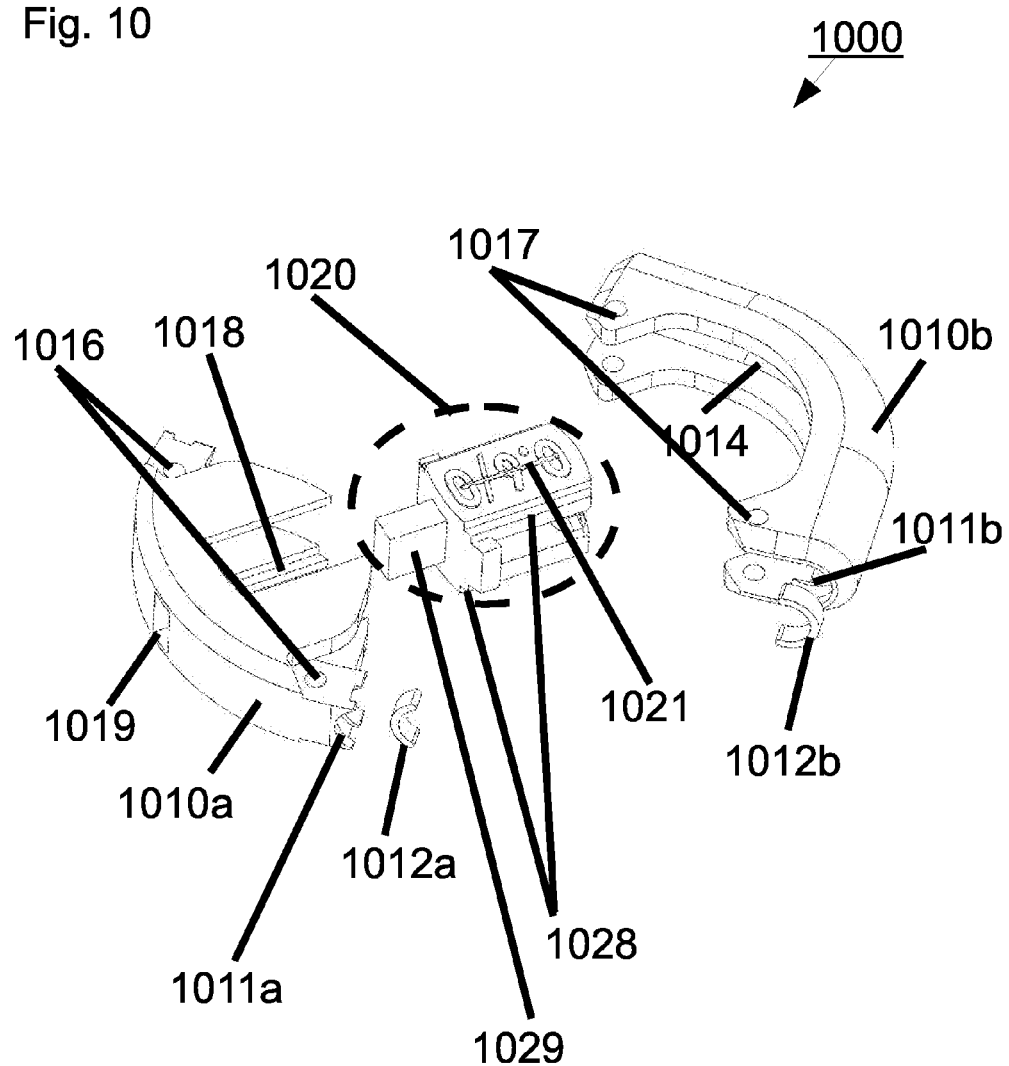
FIG. 10 is an exploded perspective view of an apparatus according to another additional exemplary embodiment of the invention.

FIG. 10 is an exploded view of an apparatus according to another additional exemplary embodiment of the invention indicated generally as 1000.

Figure 11A:
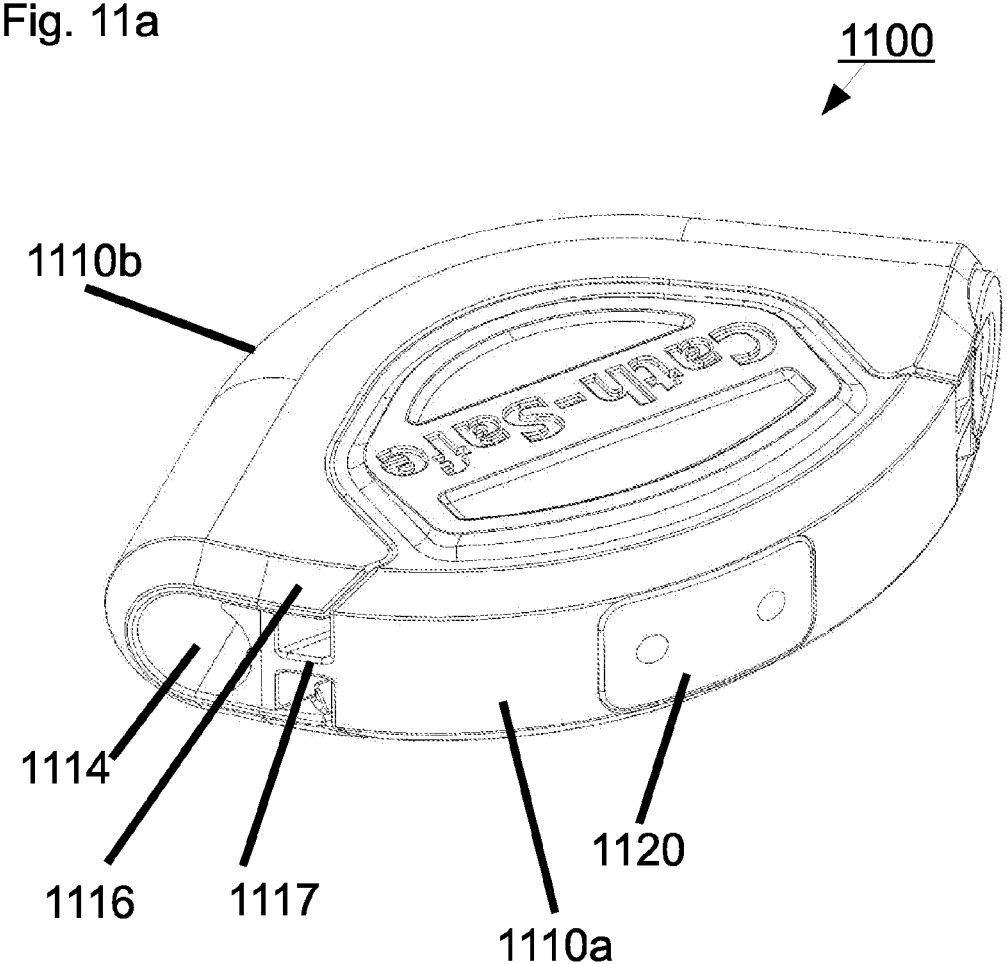
FIG. 11a is a perspective view of an apparatus according to yet another additional exemplary embodiment of the invention fully assembled (but without a catheter)

FIG. 11a is a perspective view of an apparatus according to yet another additional exemplary embodiment of the invention indicated generally as 1100.

Figure 11B:
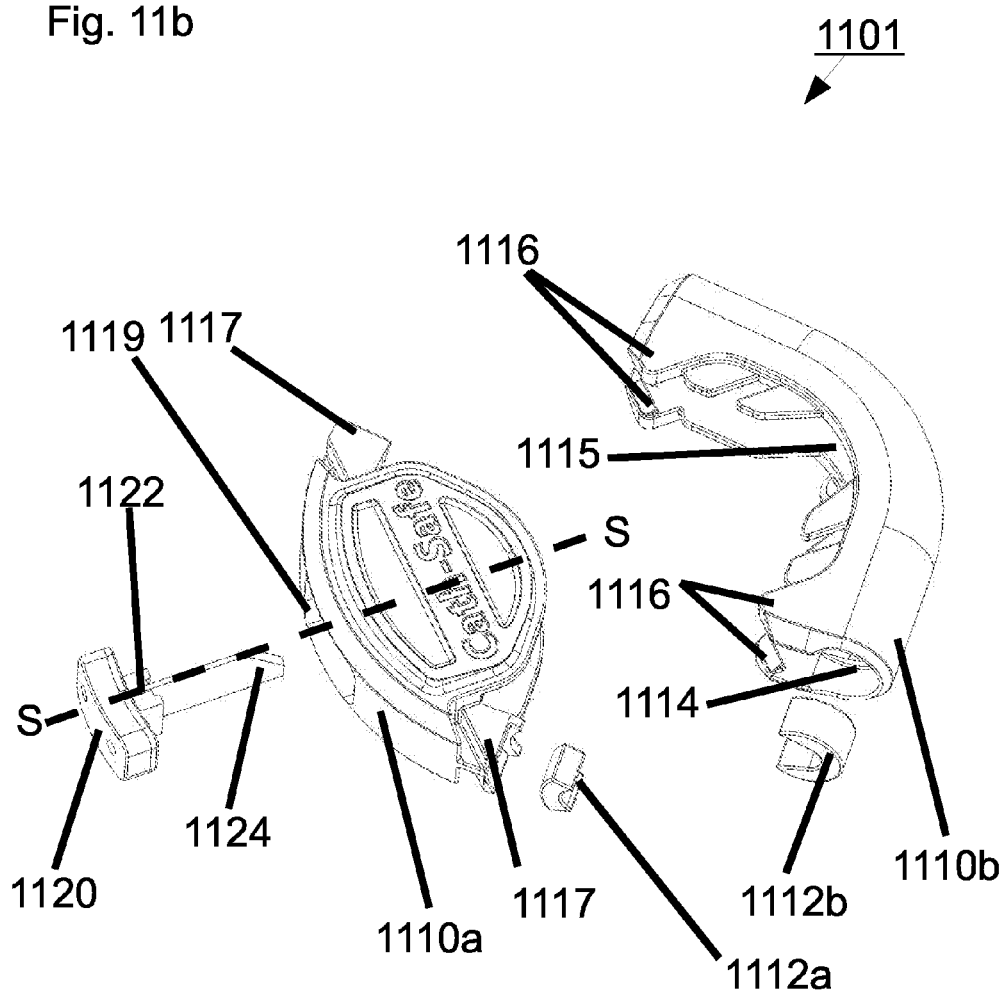

FIG. 11b is an exploded view 1101 of apparatus 1100.

FIG. 11e is a transverse cross section 1102 of 1110a along line S-S.

These additional exemplary apparatus are similar to those depicted in FIGS. 1a to 1e; 2a to 2b and 3a to 3b in that they each include a main body (e.g. 910a and 910b in FIG. 9a; 1010a and 1010b in FIGS. 10 and 1110a and 1110b in FIG. 11b) adapted to engage and retain a catheter therein at a fixed point relative to the catheter length and a cutting mechanism (e.g. 920 in FIGS. 9a and 9b; 1020 in FIG. 10 and 1120 and 1124 in FIG. 11b in conjunction with 1126a and 1126b in FIG. 11c) adapted to sever the catheter in response to a predefined threshold force applied along the length of the catheter. As with the apparatus described depicted in FIGS. 1a to 1e; 2a to 2b and 3a to 3b, in some embodiments the predefined threshold force is greater than 1.5 Kgf and/or less than 6.0 Kgf. Each of the three depicted additional exemplary apparatus employs a fixed blade (e.g. 924 in FIGS. 9a and 1124 in FIG. 11c). Alternatively or additionally, Each of the three depicted additional exemplary apparatus includes a pair of arms (e.g. 926a and 926b in FIGS. 9a and 9b and 1126a and 1126b in FIG. 11c) with an aperture between them and positioned between the fixed blade (e.g. 924 in FIGS. 9a and 1124 in FIG. 11c) and a catheter engaged and retained in the main body. Although the catheter is not depicted in the drawings it would run from the aperture formed by 911a and 911b to the aperture formed by 914a and 914b in FIG. 9a; from the aperture formed by 1011a and 1011b along the length of inner channel 1014 in FIG. 10 and from the aperture formed by 1114 along the length of inner channel 1115 in FIG. 11b.

In the depicted exemplary embodiments, (FIGS. 9a, 10 and 11b respectively) flanges 912a and 912b; 1012a and 1012b; and 1112a and 1112b form tensioning collars on the catheter when the apparatus is assembled with the catheter as in FIG. 1a. During use, the tensioning collar restricts axial translation of the main body with respect to a catheter retained therein. In some embodiments, the tensioning collar helps insure that a threshold force applied along the catheter length (e.g. as explained in the context of FIG. 1a above) results in cutting of the catheter. According to various exemplary embodiments of the invention the flanges and/or tension collars are constructed of soft materials which, when compressed between the main body and the catheter, contribute to an increase in resistance to axial translation.

In the depicted exemplary embodiments, (FIGS. 9a, 9b, 10, 11b and 11c) the apparatus includes a blade holder (e.g. 920, 1020 or 1120 in FIGS. 9a, 10 and 11b respectively) designed and configured to hold blade (e.g. 924 or 1124 in FIGS. 9a and 11b respectively) in a fixed orientation with respect to the arms (e.g. 926a and 926b; 1126a and 1126b in FIGS. 9b and 11c respectively) and with respect to main body (e.g. 910a and 910b; 1010a and 1010b; and 1110a and 1110b in FIGS. 9a, 10 and 11b respectively). Adaptations to hold blade in a fixed orientation with respect to the arms include and/or main body include but are not limited to slit 922 and/or notch 1122 and/or well 918 and/or socket 1119 and/or mating grooves 1028 and 1018. In other exemplary embodiments of the invention, (not depicted) the blade holder is produced by over-molding or insert-molding. Therefore, a slit or notch is not present in all embodiments.

In the embodiments depicted in FIGS. 9a, 9b and 10, the arms are provided as part of the blade holder In the embodiment depicted in FIGS. 11a, 11b and 11c, the pair of arms 1126a and 1126b are integrally formed with or attached to a portion of the main body 1110a. According to embodiments of this type the apparatus includes a blade holder 1120 designed and configured for insertion in a corresponding socket 1119 in main body 1110a.

In some exemplary embodiments of the invention, the apparatus includes a main body (e.g. 910a and 910b in FIG. 9a; 1010a and 1010b in FIGS. 10 and 1110a and 1110b in FIG. 11a) adapted to engage and retain a catheter therein at a fixed point relative to the catheter length and a fixed blade (e.g. 924 or 1124) and a pair of arms (e.g. 926a and 926b; 1126a and 1126b in FIGS. 9b and 11c respectively) positioned between said blade and an inner surface of said main body. A catheter engaged and retained in the main body will occupy the space between the arms and the inner surface of the main body (e.g. channel 1114), although the catheter is not part of the apparatus. The spatial relationship between the arms determines a threshold force which, when applied along the length of the catheter, causes the catheter to pass between said arms and be cut by said blade.

In some embodiments, the apparatus includes a blade holder (e.g. 920, 1020 or 1120 in FIGS. 9a, 10 and 11b respectively) designed and configured to hold the blade in a fixed orientation with respect to the arms and with respect to the main body.

In some embodiments, the pair of arms 1126a and 1126b are integrally formed with or attached to a portion 1110a of the main body and a blade holder 1120 resides within a socket 1119 in the main body. In the depicted exemplary embodiment, socket 1119 is designed and configured to engage and retain the blade holder 1120 (FIGS. 11b and 11c). In other exemplary embodiments of the invention, the main body and arms are formed around the blade and no assembly is required.

In other exemplary embodiments of the invention, the main body comprises two halves (e.g. 910a and 910b or 1010a and 1010b) and the arms (e.g. 926a and 926 b) and blade (e.g. 924) are provided as part of a core (e.g. 920 or 1020) adapted to be engaged and retained by at least one of the halves. (FIGS. 9a, 9b and 10)

Exemplary Apparatus Assembly

Referring now to FIGS. 9a and 9b:

Depicted exemplary apparatus 900 is assembled by inserting blade 924 into cutting mechanism 920 through slot 922. This fixes the orientation of the cutting edge of blade 924 with respect to arms 926a and 926b. Cutting mechanism 920 fits snugly in well 918 so that its orientation with respect to main body half 910b is fixed. Flange 912b fits in aperture half 911b. The catheter is inserted in the channel formed by flange 912b, 912a, arms 926a/926b, main body 910b and aperture half

914*b*. At this point arms 926*a*/926*b* separate the catheter from blade 924. The catheter passes between arms 926*a*/926*b* and an inner surface of main body 910*b*. Flange 912*a* is either inserted in aperture half 911*a* or positioned over the catheter at a point corresponding to 912*b*. Main body half 910*a* in fastened to main body half 910*b* so that aperture halves 911*a* and 914*a* are aligned with aperture halves 911*b* and 914*b* respectively. Assembly of aperture halves 911*a* and 911*b* creates a tensioning collar from flanges 912*a*/912*b*.

In some exemplary embodiments of the invention, flanges (912*a* and/or 912*b* and/or 1012*a* and/or 1012*b* and/or 1112*a* and/or 1112*b*) are fashioned from resilient material such as silicon, rubber, PU (Polyurethane) or TPE (Thermoplastic Polyethylene). As depicted, the flanges are sized and shaped to increase friction between the main body and a catheter installed therein.

The tensioning collar limits axial translation of the catheter and main body 910 (*a*+*b*) with respect to one another. In the depicted exemplary embodiment, snap-pins 916 mate with corresponding sockets (not depicted) in main body half 910*a*. A force applied along the length of the catheter causes the catheter to press against arms 926*a*/926*b*. When the threshold force is reached, the catheter passes through the aperture between the arms with sufficient force that it strikes blade 924 and is severed. After severing, one half of the catheter can slide through aperture 914(*a*+*b*) in response to force well below the threshold force while the second half of the catheter is retained by tensioning collar 912(*a*+*b*).

In some exemplary embodiments of the invention, the apparatus is assembled so that the tensioning collar is proximal to the patient. According to these embodiments, if severing of the catheter causes deflation of balloon 91 (FIG. 1), device 900 prevents the severed end of the catheter from moving into the urethra.

In other exemplary embodiments of the invention, the apparatus is assembled so that the tensioning collar is distal to the patient.

Referring now to FIG. 10:

Depicted exemplary apparatus 1000 is assembled by inserting a blade (not depicted) into cutting mechanism 1020 via slit 1021. In other exemplary embodiments of the invention, cutting mechanism 1020 is produced by over-molding onto a blade. This fixes the orientation of the cutting edge of the blade with respect to a pair of arms (not depicted) in mechanism 1020. A protrusion 1029 on cutting mechanism 1020 fits snugly in socket 1019 so that its orientation with respect to main body half 1010*a* is fixed. Alternatively or additionally, mating grooves 1028 and 1018 orient mechanism 1020 with respect to main body half 1010*a*. Flanges 1012*a* and 1012*b* fit in aperture halves 1011*a* and 1011*b* respectively. In the depicted exemplary embodiment, 1011*b* includes a retention ridge which limits motion of flange 1012*b* into main body 1010*b*. The catheter is inserted in channel 1014 along its length. Main body half 1010*a* is fitted to main body half 1010*b* so that the arms in mechanism 1020 separate the catheter from the blade. Assembly of aperture halves 1011*a* and 1011*b* creates a tensioning collar from flanges 1012*a*/1012*b*. The tensioning collar limits axial translation of the catheter and main body 1010(*a*+*b*) with respect to one another. In the depicted exemplary embodiment, snap-pins 1016 mate with corresponding sockets 1017 in main body half 1010*b*. A force applied along the length of the catheter causes the catheter to press against the arms in mechanism 1020. When the threshold force is reached, the catheter passes through the aperture between the arms with sufficient force that it strikes the blade in mechanism 1020 and is severed. Behavior of the catheter after severing is similar to what is described for apparatus 900.

In exemplary embodiments in which the cutting mechanism (e.g. 920 or 1020) is prepared separately from the main body it a universal main body can be fitted with cutting mechanisms configured for different catheter diameters and/or catheter materials. This means that a manufacturing plant might have one set of molds for main body components and multiple different molds for cutting mechanisms configured for different catheters. Alternatively or additionally, in some embodiments an apparatus kit includes main body parts and a plurality of cutting mechanisms configured for different catheter sizes and/or different catheter materials. In some embodiments, the kit components are color coded. In some embodiments, the color coding matches color coding on corresponding catheters.

In some embodiments, a portion of the apparatus (e.g. 1010*b*) is constructed of a translucent or transparent material to allow medical personnel and/or caregivers to ascertain whether the catheter has been severed.

Referring now to FIGS. 11*a*, 11*b* and 11*e*:

Depicted exemplary apparatus 1100 is assembled by inserting a blade 1124 into a blade holder 1120. According to various exemplary embodiments of the invention insertion is performed manually or by a machine configured for that purpose. In other exemplary embodiments of the invention, over-molding or insert injection of the blade produce a bade holder with an integrated blade obviating a need for insertion.

Holder 1120 is seated in socket 1119. This fixes the orientation of the cutting edge of blade 1124 with respect to a pair of arms 1126*a* and 1126*b* (FIG. 11*c*) in mechanism 1120. In the depicted exemplary embodiment, the cutting mechanism is formed by assembly of blade 1124, holder 1120 and main body half 1110*a* including the arms. Assembly of the cutting mechanism fixes the orientation of the cutting edge of blade 1124 with respect to arms 1126*a* and 1126*b* as well as main body half 1110*a*. Flange 1112*b* fits in aperture half 1114. The catheter is inserted in channel 1115 along its length. Flange 1112*a* is applied to the catheter opposite flange 1112*b*. Main body half 1110*a* is fitted to main body half 1110*b* so that protrusions 1117 mate with snap wings 1116. Fitting of the main body halves together forms a tensioning collar from flanges 1112*a*/1112*b*. The tensioning collar functions as in the two previous embodiments. A force applied along the length of the catheter causes the catheter to press against arms 1126*a* and 1126*b*. When the threshold force is reached, the catheter passes through the aperture between the arms with sufficient force that it strikes blade 1124 and is severed. Behavior of the catheter after severing is similar to what is described for apparatus 900.

In some embodiments, a portion of the apparatus (e.g. 1110*b*) is constructed of a translucent or transparent material to allow medical personnel and/or caregivers to ascertain whether the catheter has been severed.

Referring now to FIG. 11*c*:

Cross section 1102 (through line S-S) illustrates most clearly how arms 1126*a* and 1126*b* define an aperture having dimensions H and L. According to various exemplary embodiments of the invention the aperture between the two arms contributes to the threshold force required to sever the catheter.

In some embodiments, the apparatus is configured for a latex catheter of 16 Fr (5.33 mm) (mm=Fr/3). According to these embodiments H=0.6 mm and L=1 mm. In some embodiments, the relationship between H and L contributes to an angle with which the catheter strikes blade 1124. Alternatively or additionally, in some embodiments the distance defined by H and L contributes to a force with which the catheter strikes blade 1124.

In other exemplary embodiments of the invention, in order to configure for a catheter with a higher Fr, H and/or L are increased. Conversely in order to configure for a catheter with a lower Fr, H and/or L are decreased.

Alternatively or additionally, in some embodiments the apparatus is configured for use with a silicon catheter. For a silicon catheter the distance defined by H and L will be different than for a latex catheter of the same Fr.

This description of the aperture and how H and/or L contribute to function of the cutting mechanism applies also to arms 926a/926b in FIGS. 9a and 9b as well as to the (undepicted) arms in cutting mechanism 1020 (FIG. 10).

Exemplary Testing Apparatus

FIGS. 12a and 12b are side views of exemplary testing apparatus indicated generally as 1200 and 1202 respectively. These apparatus allow a product developer to rapidly and easily determine configuration parameters for a desired threshold force ease.

Apparatus 1200 and 1202 each have a blade holder 1210 with a blade 1212 installed therein. In the depicted exemplary embodiments, a position of blade 1212 within holder 1210 is adjustable by manipulation of a calibrated blade adjustment knob 1220 which operates a blade adjustment mechanism 1222 (e.g. threaded post).

Depicted exemplary apparatus 1200 is designed and configured for development of apparatus of the general type depicted in FIGS. 9a, 9b, 10, 11a and 11b. Apparatus 1200 includes a first calibrated arm adjustment knob 1230 which operates a first arm adjustment mechanism 1232 (e.g. threaded post) operable to adjust displacement of a first arm 1234 in the "L" direction and a second calibrated arm adjustment knob 1240 which operates a second arm adjustment mechanism 1242 (e.g. threaded post) operable to adjust displacement of a second arm 1244 in the "H" direction.

Depicted exemplary apparatus 1202 is designed and configured for development of apparatus of the general type depicted in FIGS. 3a and 3b. Apparatus 1202 includes a pin well 1252 in which a break-away pin 1250 can be seated. Changing the diameter and/or material of pin 1250 seated in pin well 1252 will change the threshold force required to break the pin.

During use of apparatus 1200 and/or 1202, a catheter 1260 (depicted in cross section) is attached to a measurement device (e.g. spring scale; not depicted) at one end. Application of force along the catheter length (e. g. by manual pulling) causes catheter 1260 to press against the aperture between arms 1234 and 1244 (FIG. 12a) or pin 1250 (FIG. 12b). The measurement device indicates the applied force.

In apparatus 1200 H and L can be adjusted until a desired threshold force is achieved. The relevant distances can be read from calibrated knobs 1230 and 1240 and used as manufacturing parameters.

In apparatus 1202 pins 1250 of varying diameters are tried until a desired threshold force is achieved. The determined pin diameter is then used in manufacturing. The process can be repeated for pins of different materials if desired.

Depicted exemplary apparatus 1200 and 1202 permit adaptation of existing catheter add-ons to catheters with different diameters and/or adaptation of existing catheter add-ons to catheters constructed of different materials.

Exemplary Moving Blade Apparatus

Figure 4A:
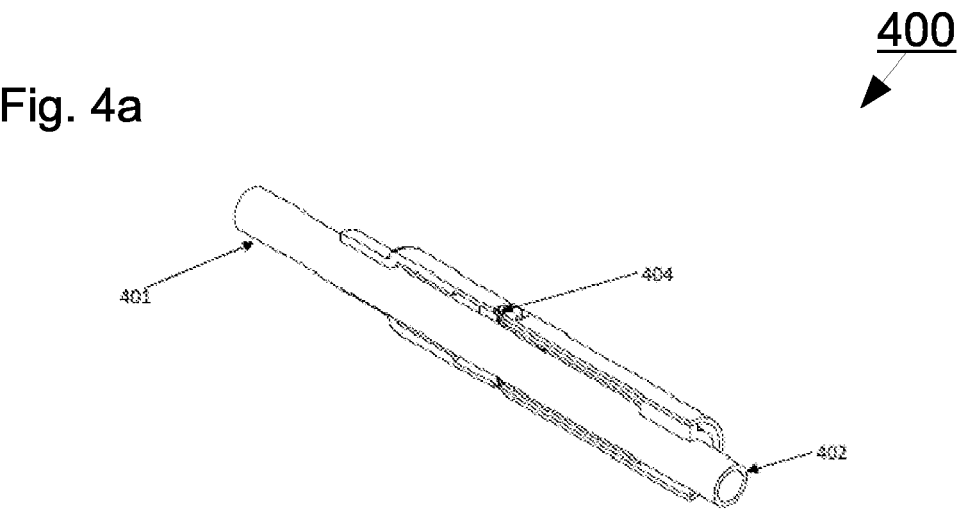
FIG. 4a is a perspective view of a half of an apparatus according to still further additional embodiments of the invention installed on a catheter.

FIG. 4a is a perspective view of a half of an apparatus, indicated generally as 400, according to still further additional embodiments of the invention installed on a catheter. In the drawing, 401 and 402 correspond to 101 and 102 in FIG. 1a respectively.

Figure 4B:
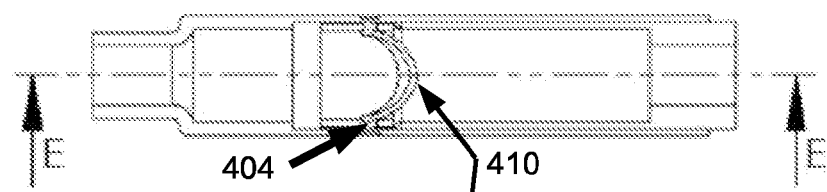
FIG. 4b is cut away view of the apparatus as depicted in FIG. 4a with functional components exposed.

FIG. 4b is cut away view of the apparatus as depicted in FIG. 4a with functional components exposed.

Figure 4C:
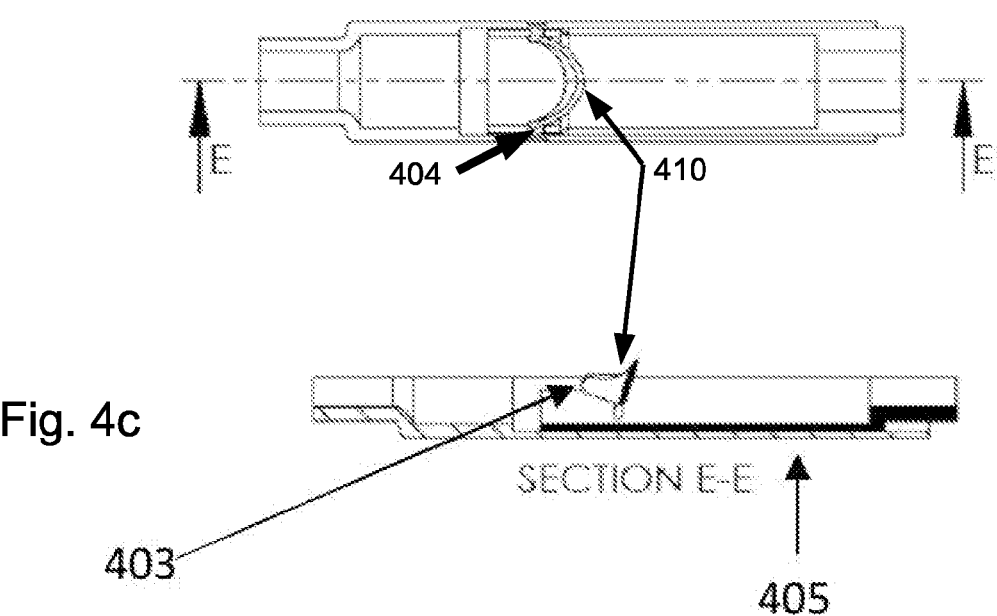
FIG. 4c is a section cut through line E-E of FIG. 4b with cutting mechanism activated.

FIG. 4c is a section cut through line E-E of FIG. 4b with cutting mechanism activated.

Figure 4D:
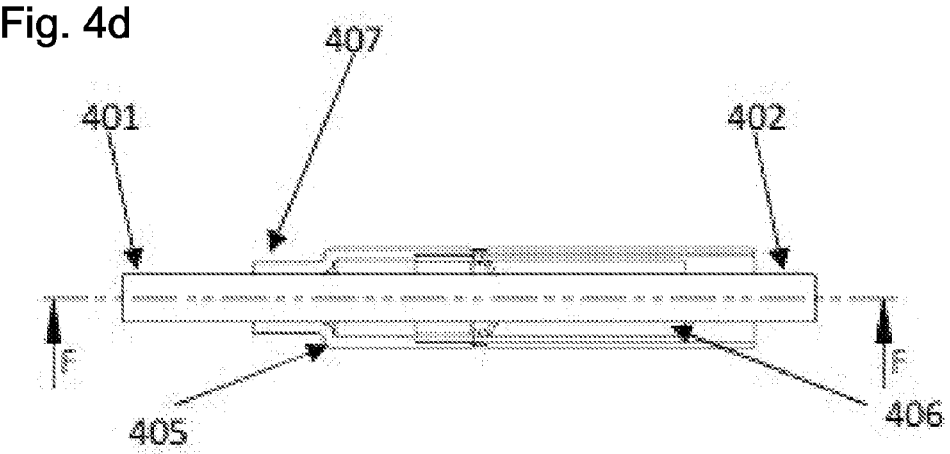
FIG. 4d is a cut away view of the apparatus as depicted in FIG. 4a installed upon a catheter.

FIG. 4d is a cut away view of the apparatus as depicted in FIG. 4a installed upon a catheter.

Like the embodiments described hereinabove, apparatus 400 severs a catheter upon which it is installed in response to a predetermined threshold force applied along the length of the catheter. In depicted apparatus 400, the main body (FIG. 4e) includes a distal portion 405 which remains on the distal portion of the catheter after cutting and a proximal portion 406 which remains on the proximal portion of the catheter after cutting. In the depicted exemplary embodiment, adhesive edge 407 holds portion 405 of the housing to the catheter. In the depicted exemplary embodiment, portion 406 of the housing is at least partially inserted within portion 405 of the housing. Inner portion 406 is connected to one or more blades 410 by a hinge 404 (FIG. 4b). Application of force along the length of the catheter causes motion of housing portion 406 away from housing portion 405 which causes the cutting edge of blade(s) 410 to swing towards the catheter (by rotation around hinge 404). When the threshold force is reached, blade(s) 410 sever the catheter. In other words, one or more blades 410 swing away from an inner wall of portion 405 of the main body so that a cutting surface contacts a catheter passing through the main body.

Additional Exemplary Moving Blade Apparatus

Figure 5A:
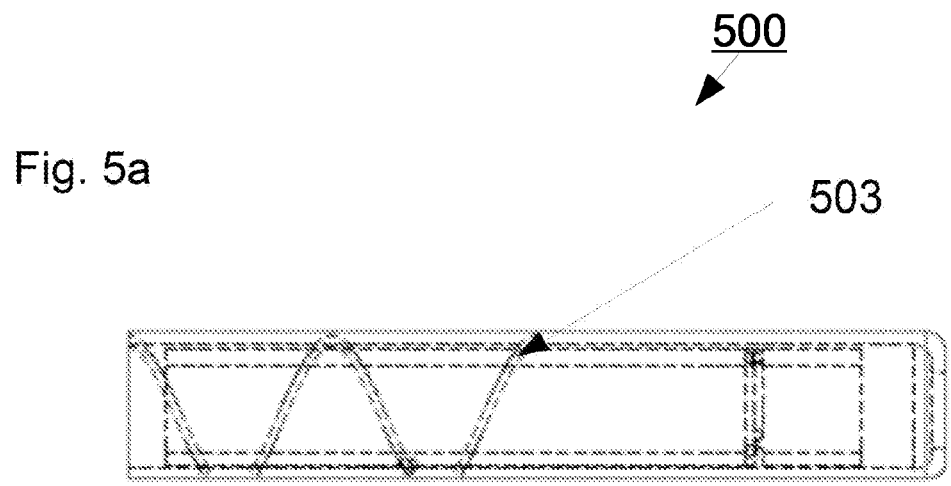
FIG. 5a is a side view of an apparatus according to another exemplary embodiment of the invention with dashed lines indicating a circular mechanism.

FIG. 5a is a side view of an apparatus indicated generally as 500, according to still further additional embodiments of the invention with dashed lines indicating a circular mechanism.

Figures 5B, 5C:
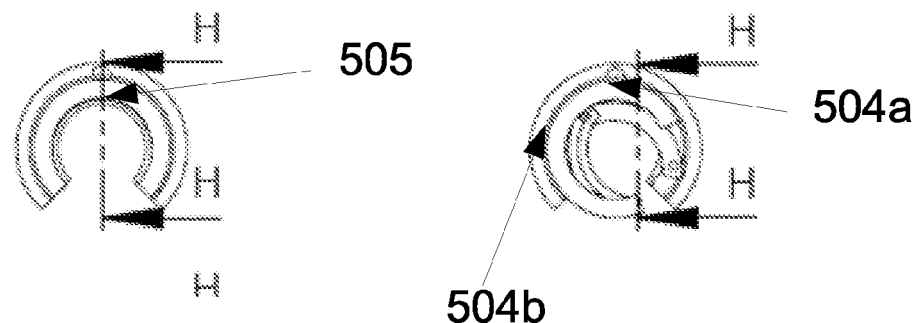
FIG. 5b is a transverse cross section of the apparatus of FIG. 5a at line H-H with blades open (ready mode)
FIG. 5c is a transverse cross section of the apparatus of FIG. 5a at line H-H with blades closed (cutting mode)
Figure 5D:
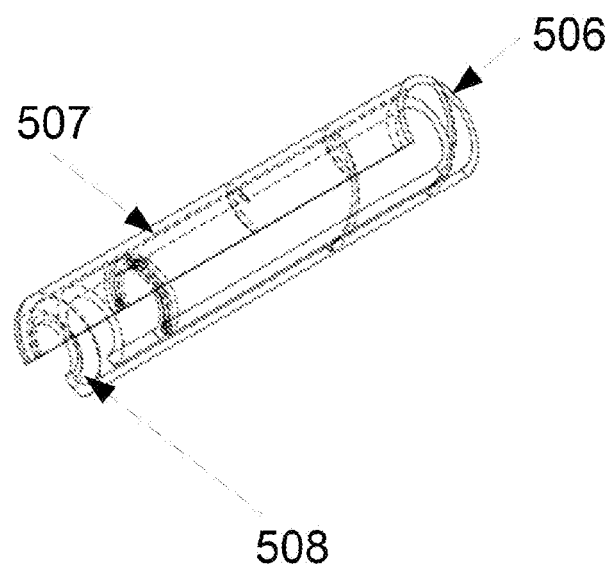
FIG. 5d is an isometric view of the apparatus of FIG. 5a with blades open.
Figure 5E:
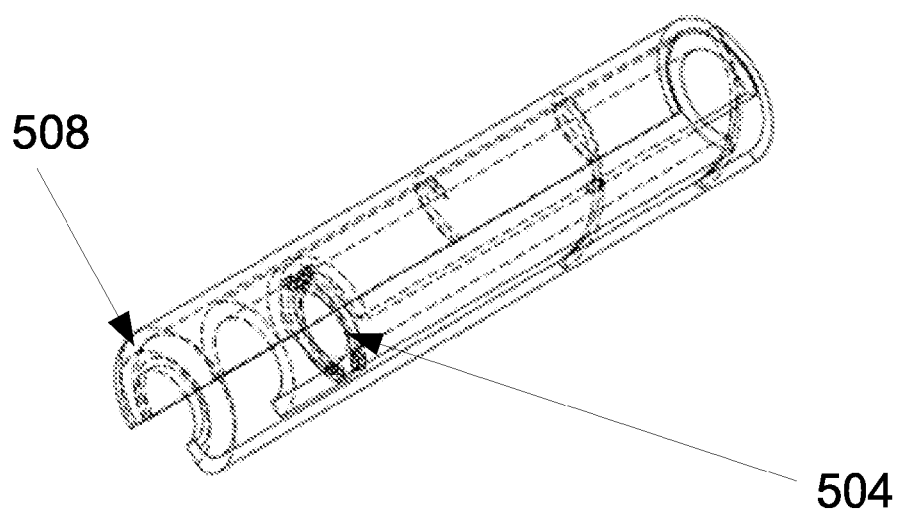
FIG. 5e is an isometric view of the apparatus of FIG. 5a with blades closed.

FIG. 5b is a transverse cross section of the apparatus of FIG. 5a at line H-H with blades open (ready mode);

FIG. 5c is a transverse cross section of the apparatus of FIG. 5a at line H-H with blades closed (cutting mode);

FIG. 5d is an isometric view of the apparatus of FIG. 5a with blades open;

FIG. 5e is an isometric view of the apparatus of FIG. 5a with blades closed;

In the depicted exemplary embodiment, two or more blades 504 with cutting surfaces which move towards one another in response to application of the pre-defined threshold force.

Two tubular elements 506 and 507 (FIG. 5d) placed one inside the other with circular mechanism 503 (FIG. 5a) between them. The inner tube is connected to a hinge 505 and two blades 504a and 504b. The inner tube 506 and the outer tube 507 are mounted by adhesive 508 to the catheter. By pulling of the catheter the linear motion of 506 with respect to 507 is transformed to rotary motion by circular mechanism 503. This rotary motion is transferred to a hinge 505 which causes blades 504a and 504b to sever the catheter in a scissor like motion.

Exemplary Method of Manufacture

Figure 6:
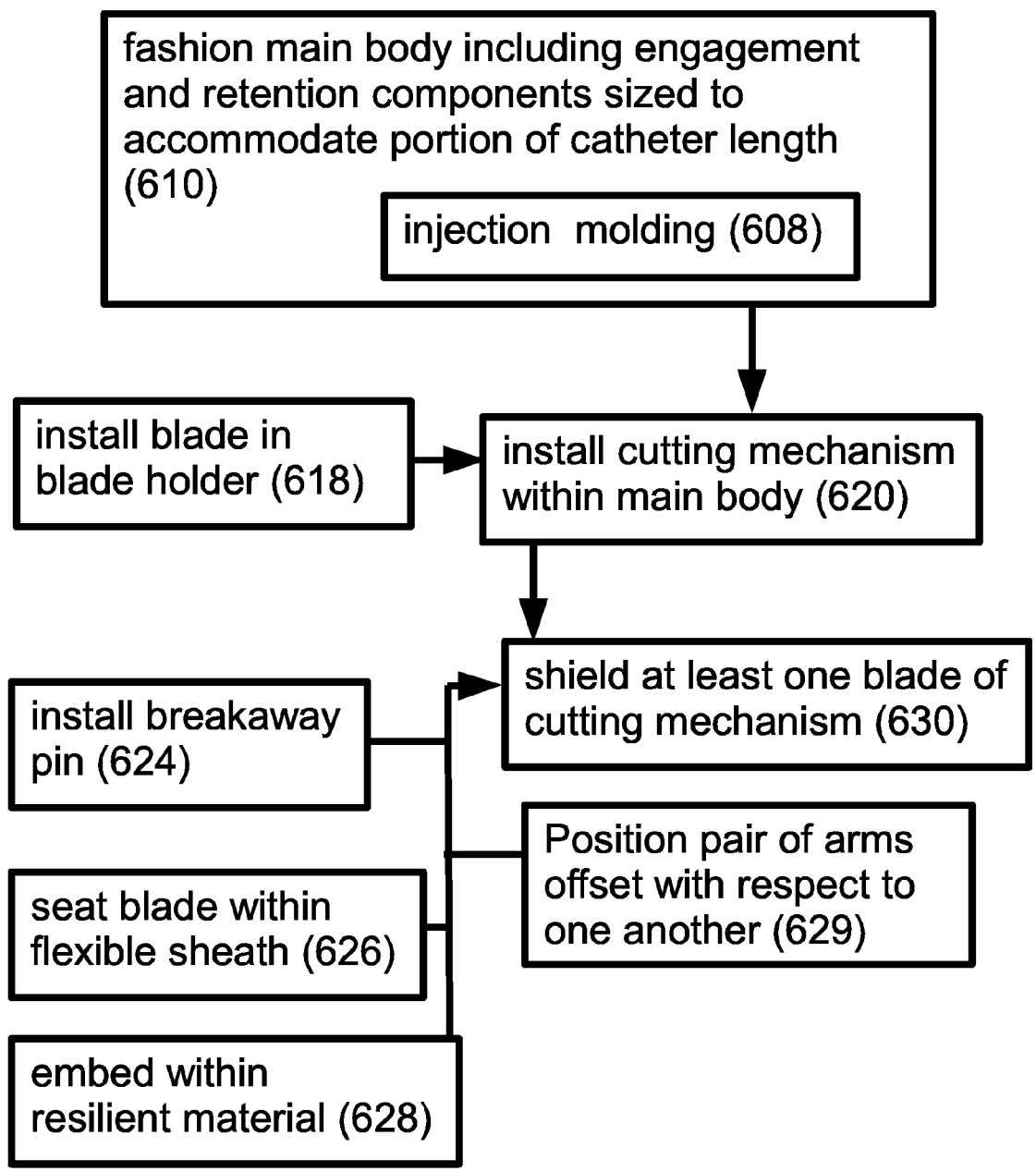
FIG. 6 is a simplified flow diagram of a method of manufacture according to some embodiments of the invention.

FIG. 6 is a simplified flow diagram of a method of manufacture according to some embodiments of the invention indicated generally as 600.

Depicted exemplary method 600 includes fashioning 610 a main body including engagement and retention components sized to accommodate a portion of a catheter length. In some embodiments, fashioning 610 includes fashioning a socket or well designed and configured to engage and retain a blade holder in the main body.

The depicted embodiment includes installing 620 a cutting mechanism within the main body. In some embodiments, installing 620 includes attachment of one or more blades. In some embodiments, installation 620 of the cutting mechanism includes installing 618 a blade in a blade holder (e.g. blade 924 in slit 922 or blade 1124 in notch 1122). In some embodiments, the method includes inserting the blade holder in a socket or well in the main body.

In some embodiments, fashioning 610 includes injection molding and/or thermo-forming and/or milling and/or additive manufacturing (also known as 3D printing) and/or over molding and/or co-injection and/or insertion molding.

In some exemplary embodiments of the invention, blades and/or a breakaway pin are installed as part of the injection process, for example, by over molding.

In other exemplary embodiments of the invention, fashioning 610, installing 620 and installing 618 are integrated into a single process using over mold injection.

In some embodiments installing 620 is an integral part of fashioning 610. In some embodiments, method 600 includes shielding 630 at least one blade of the cutting mechanism. Shielding prevents contact between the cutting surface of the blade and the catheter until force is applied and/or shields from the patient and/or the medical staff working with the apparatus. According to various exemplary embodiments of the invention shielding 630 includes embedding 628 within a resilient material and/or seating 626 the at least one blade within a flexible sheath and/or installing 624 a breakaway pin and/or positioning 629 positioning a pair of arms offset with respect to one another in at least two different dimensions between a blade of said cutting mechanism and said engagement and retention components. In some exemplary embodiments of the invention, injection molding 608 performs the positioning of the arms.

In some embodiments, the breakaway pin serves as part of the engagement and retention components. Alternatively or additionally, in some embodiments fashioning 610 produces two pieces configured to axially translate with respect to one another.

In some embodiments, method 600 includes enclosing the main body with the cutting mechanism installed in sterilizable packaging material. In some embodiments, method 600 includes sterilizing the package. Alternatively or additionally, in some embodiments a catheter compatible with the main body/cutting mechanism is enclosed in the same package. Optionally, the main body is installed upon the catheter prior to enclosing in the packaging material.

Exemplary Treatment Method

FIG. 7 is a simplified flow diagram of a method of treatment, indicated generally as 700, according to some embodiments of the invention.

Depicted exemplary method 700 includes inserting 710 an in-dwelling urinary catheter into a bladder of a patient via the urethra, inflating 720 a balloon at the end of the catheter in the bladder and installing 730 a apparatus comprising a cutting mechanism responsive to a pre-defined threshold force applied along the length of the catheter at a point on the catheter adjacent to the urethra. In this context, "adjacent to" means not enough catheter is left exposed between the apparatus and the urethra for a patient to easily grasp. In some embodiments, the pre-defined threshold force is greater than 1.5 Kgf or is greater than 2.0 Kgf. Alternatively or additionally, in some embodiments the pre-defined threshold force is less than 5.0 Kgf.

Exemplary Assembly Method

FIG. 8 is a simplified flow diagram of a method of assembly, indicated generally as 800, according to some embodiments of the invention. Depicted exemplary method 800 includes providing 810 a catheter and installing 820 an apparatus comprising a cutting mechanism responsive to a pre-defined threshold force applied along the length of the catheter at a fixed point on the catheter. In some embodiments, the pre-defined threshold force is greater than 1.5 Kgf or is greater than 2.0 Kgf. Alternatively or additionally, in some embodiments the pre-defined threshold force is less than 5.0 Kgf.

Exemplary Materials

According to various exemplary embodiments of the invention the main body of the apparatus and/or the blade holder is constructed of metal and/or polymeric plastics and/or ceramic materials. In some exemplary embodiments of the invention, the main body is constructed of plastic and the blade is constructed of metal and/or ceramic material.

Suitable metals include, but are not limited to steel, aluminum and aluminum alloys.

Suitable polymeric plastics include, but are not limited to thermoplastic materials including but not limited to ABS (Acrylonitrile-Butadiene-Styrene (Terpolymer)), PC-ABS (Polycarbonate/Acrylonitrile Butadiene Styrene), PU (polyurethane), PE (polyethylene), PP (polypropylene), PETG (Polyethylene Terephthalate Glycol), PET (Polyethylene Terephthalate), PC (polycarbonate), PA (polyamide), PS (polystyrene), PVC (polyvinylchloride) and POM (polyoxymethylene).

According to various exemplary embodiments of the invention the blade is constructed of materials including, but not limited to Stainless steel and/or Razor Blade steel and/or Carbon Steel and/or Chrome Steel.

Alternatively or additionally, according to various exemplary embodiments of the invention flanges (e.g. 912a/912b; 1012a/1012b and 1112a/1112b) are constructed of resilient material such as silicon and/or rubber and/or PU (polyurethane) and/or TPE (thermoplastic polyethylene).

Exemplary Technical Specification

In some embodiments, apparatus according to various configurations described hereinabove have a total weight of about 50 g, about 40 g, about 30 g, about 20 or about 10 g or intermediate or lesser weights. In some embodiments, a reduction in weight contributes to a reduction in the probability of patient discomfort or other adverse reaction.

In some embodiments, apparatus according to various configurations described hereinabove have overall dimensions of 20 mm×50 mm×20 mm or less.

In some embodiments, apparatus according to various configurations described hereinabove have overall dimensions of 45 mm×30 mm×12 mm or less.

In some embodiments, apparatus according to various configurations described hereinabove do not affect rate of flow of urine between the bladder and urine collecting bag by more than about 2%. Rate of flow is typically about 2.22 cc/sec on 16 Fr lumen catheters with normal kidney function.

In some embodiments, apparatus according to various configurations described hereinabove have cutting mechanisms described hereinabove which operate in an "all or nothing" fashion (i.e. there is no partial cutting prior to application of threshold tension).

Exemplary Use Considerations

Although various embodiments of the apparatus described above are different in design, they are all easily installed by anyone that is accustomed to installing catheters. Training, if any is needed, should take only a few minutes. In many cases a single demonstration is enough. In other cases, no training is needed and the apparatus comes with installation instructions. In some embodiments, these instructions include a series of line drawings or photographs.

In some embodiments, the apparatus is removable by one person and without causing damage to the catheter or the patient (i.e. pulling the device while being catheter installed). Alternatively or additionally, in some embodiments the apparatus is removable without tools.

Alternatively or additionally, in some embodiments the apparatus does not 'travel' over the catheter length but can be manually adjusted to a desired point along the catheter length after placement.

In some embodiments, the apparatus has a place for writing time/date of installation and installer name.

It is expected that during the life of this patent many new catheter types will be developed and the scope of the invention is intended to include all such new technologies a priori.

As used herein the term "about" refers to ±10%.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Specifically, a variety of numerical indicators have been utilized. It should be understood that these numerical indicators could vary even further based upon a variety of engineering principles, materials, intended use and designs incorporated into the various embodiments of the invention. Additionally, components and/or actions ascribed to exemplary embodiments of the invention and depicted as a single unit may be divided into subunits. Conversely, components and/or actions ascribed to exemplary embodiments of the invention and depicted as sub-units/individual actions may be combined into a single unit/action with the described/depicted function.

Alternatively, or additionally, features used to describe a method can be used to characterize an apparatus and features used to describe an apparatus can be used to characterize a method.

It should be further understood that the individual features described hereinabove can be combined in all possible combinations and sub-combinations to produce additional embodiments of the invention. The examples given above are exemplary in nature and are not intended to limit the scope of the invention which is defined solely by the following claims.

Each recitation of an embodiment of the invention that includes a specific feature, part, component, module or process is an explicit statement that additional embodiments not including the recited feature, part, component, module or process exist.

Specifically, the invention has been described in the context of Foley catheters but might also be used with a wide variety of other catheter types for different medical purposes.

All publications, references, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The terms "include", and "have" and their conjugates as used herein mean "including but not necessarily limited to".

The invention claimed is:

1. An apparatus comprising:
   (a) a main body adapted to engage and retain a catheter therein at a fixed point relative to the catheter length; and
   (b) a cutting mechanism adapted to sever said catheter in response to a predefined threshold force applied along the length of the catheter;
   wherein the apparatus lacks a spring.

2. An apparatus according to claim 1, wherein said cutting mechanism employs a fixed blade.

3. An apparatus according to claim 2, comprising a pair of arms with an aperture between them, said aperture positioned between said fixed blade and a catheter engaged and retained in said main body.

4. An apparatus according to claim 3, comprising a blade holder designed and configured to hold said blade in a fixed orientation with respect to said arms and with respect to said main body.

5. An apparatus according to claim 3, wherein said pair of arms are integrally formed with or attached to a portion of said main body, and comprising a blade holder designed and configured for insertion in a corresponding socket in said main body.

6. An apparatus according to claim 2, wherein said fixed blade is embedded within a resilient material.

7. An apparatus according to claim 2 wherein said fixed blade is separated from said catheter by a break-away pin when said catheter is engaged and retained by said main body.

8. An apparatus according to claim 1, wherein said cutting mechanism includes one or more blades which move in response to application of the threshold force.

9. An apparatus according to claim 1, comprising a tensioning collar adapted to restrict axial translation of said main body with respect to a catheter retained therein.

10. A method comprising:
    (a) fashioning a main body including engagement and retention components sized to accommodate a portion of a catheter length; and
    (b) installing a cutting mechanism within said main body, to produce a device with no spring.

11. A method according to claim 10, wherein said fashioning includes at least one process selected from the group consisting of injection molding, co-injection, insert injection and over molding.

12. A method according to claim 10, wherein said fashioning includes additive manufacturing.

13. A method according to claim 10, comprising shielding at least one blade of said cutting mechanism.

14. A method according to claim 13, wherein said shielding includes positioning a pair of arms offset with respect to one another in at least two different dimensions between a blade of said cutting mechanism and said engagement and retention components.

15. A method according to claim 13, wherein said shielding includes installing a breakaway pin.

16. A method according to claim 10, wherein said installing includes attachment of one or more blades.

17. A method according to claim 10, comprising enclosing said main body with said cutting mechanism installed in sterilizable packaging material.

18. A method of treatment comprising:
    (a) inserting an in-dwelling urinary catheter into a bladder of a patient via the urethra;
    (b) inflating a balloon at the end of the catheter in the bladder; and (c) installing an apparatus comprising a cutting mechanism responsive to a pre-defined threshold force applied along the length of the catheter at a point on the catheter adjacent to the urethra.

19. A method according to claim 18, wherein said pre-defined threshold force is greater than 1.5 Kgf.

20. A method according to claim 18 or 19, wherein said pre-defined threshold force is less than 5.0 Kgf.

* * * * *